(12) United States Patent
Lu et al.

(10) Patent No.: US 12,351,819 B2
(45) Date of Patent: Jul. 8, 2025

(54) METHOD FOR REMOVING UNDIFFERENTIATED PLURIPOTENT STEM CELLS

(71) Applicants: Joyce Jean Lu, Taipei (TW); ACADEMIA SINICA, Taipei (TW)

(72) Inventors: Joyce Jean Lu, Taipei (TW); Yu-Tsen Lin, Taipei (TW)

(73) Assignee: ACADEMIA SINICA, Taipei (TW)

( * ) Notice: Subject to any disclaimer, the term of this patent is extended or adjusted under 35 U.S.C. 154(b) by 1312 days.

(21) Appl. No.: 16/620,395

(22) PCT Filed: Jun. 6, 2018

(86) PCT No.: PCT/US2018/036213
§ 371 (c)(1),
(2) Date: Dec. 6, 2019

(87) PCT Pub. No.: WO2018/226797
PCT Pub. Date: Dec. 13, 2018

(65) Prior Publication Data
US 2021/0147796 A1 May 20, 2021

Related U.S. Application Data

(60) Provisional application No. 62/516,437, filed on Jun. 7, 2017.

(51) Int. Cl.
| | | |
|---|---|---|
| *C12N 5/00* | (2006.01) | |
| *A61K 31/585* | (2006.01) | |
| *A61K 31/7048* | (2006.01) | |
| *A61P 35/00* | (2006.01) | |
| *C07D 307/04* | (2006.01) | |
| *C12N 5/0735* | (2010.01) | |
| *C12N 5/0775* | (2010.01) | |

(52) U.S. Cl.
CPC .......... *C12N 5/0081* (2013.01); *C07D 307/04* (2013.01); *C12N 5/0668* (2013.01); *A61K 31/585* (2013.01); *A61K 31/7048* (2013.01); *A61P 35/00* (2018.01); *C12N 5/0606* (2013.01)

(58) Field of Classification Search
CPC .............. A61K 31/7048; A61K 31/585; C12N 5/0606; C12N 5/0668; C12N 5/0081; A61P 35/00; C07D 307/04
See application file for complete search history.

(56) References Cited

U.S. PATENT DOCUMENTS

| | | | | |
|---|---|---|---|---|
| 8,685,726 | B2 * | 4/2014 | Schulz | C12N 5/0606 435/405 |
| 2013/0261142 | A1 * | 10/2013 | Lai | A61K 31/13 514/622 |
| 2014/0011755 | A1 * | 1/2014 | Stein | A61K 31/7048 514/26 |
| 2015/0148359 | A1 * | 5/2015 | Ben-David | A61K 31/513 514/354 |

OTHER PUBLICATIONS

Narsinh et al. Comparison of Human Induced Pluripotent and Embryonic Stem Cells: Fraternal or Identical Twins? Molecular Therapy (2011), v19(4), p. 635-638. (Year: 2011).*
Barrand et al. Chromatin states of core pluripotency-associated genes in pluripotent, multipotent and differentiated cells. Biochemical and Biophysical Research (2010), 391, 762-787. (Year: 2010).*
Roobrouck et al. Concise Review: Culture Mediated Changes in Fate and/or Potency of Stem Cells. Stem Cells (2011), v29(4), p583-589. (Year: 2011).*
Cheng et al. Application of Mouse Embryonic Stem Cell Test to Detect Gender-Specific Effect of Chemicals: A Supplementary Tool for Embryotoxicity Prediction. Chem. Res. Toxicol. (Jul. 2016), 29, 1519-1533. (Year: 2016).*
Nery et al. Human Mesenchymal Stem Cells: From Immunophenotyping by Flow Cytometry to Clinical Applications. Cytometry Part A (2012), 83A, 48-61. (Year: 2012).*
Koh et al. Identification of Na+/K+- ATPase inhibition-independent proarrhythmic ionic mechanisms of cardiac glycosides. Scientific Reports (May 2017), 7:2465. (Year: 2017).*
Cheng et al. Application of Mouse Embryonic Stem Cell Test to Detect Gender-Specific Effect of Chemicals: A Supplementary Tool for Embryotoxicity Prediction. Chemical Research in Toxicology (Jul. 2016), 29, 1519-1533. (Year: 2016).*
International Search Report for PCT/US2018/036213 mailed on Sep. 26, 2018.
Lee et al., "Inhibition of pluripotent stem cell-derived teratoma formation by small molecules", Aug. 5, 2013, PNAS, vol. 110, Issue 35, pp. E3281-E3290.
Lin et al., "Elimination of undifferentiated human embryonic stem cells by cardiac glycosides". Jul. 13, 2017, Scientific Reports, vol. 7, No. 5289, pp. 1-12.
Winnicka et al., "Cardiac Glycosides in Cancer Research and Cancer Therapy", Mar. 1, 2006, Acta Poloniae Pharmaceutica - Drug Research, vol. 63, No. 2, pp. 109-115.
Written Opinion of the International Searching Authority for PCT/US2018/036213 mailed on Sep. 26, 2018.

* cited by examiner

*Primary Examiner* — Sean C. Barron
(74) *Attorney, Agent, or Firm* — Birch, Stewart, Kolasch & Birch, LLP

(57) ABSTRACT

The present invention relates to a method for removing undifferentiated embryonic stem cells. In particular, the present invention relates to a method for removing undifferentiated embryonic stem cells by using cardiac glycosides (CGs). The present invention also relates to a method for preparing differentiated cells in which undifferentiated embryonic stem cells have been removed and a method for cell therapy by using such differentiated cells.

11 Claims, 26 Drawing Sheets

Method:
Stem Cells, 2015 [Epub ahead of print]

| Positive marker | | Negative marker cocktail | |
|---|---|---|---|
| CD44 | 99.9% | CD45/CD34/CD11b/CD19/HLA-DR | 0.57% |
| CD73 | 100.0% | | |
| CD90 | 93.8% | | |
| CD105 | 99.0% | | |

Fig. 8C

TUJ1/DAPI

AFP/DAPI

Digoxin

Lanatoside C

| CGs | IC50 (µM) |
|---|---|
| Digoxin | 0.10 |
| Lanatoside C | 0.15 |
| Proscillaridin A | 0.20 |
| Digitoxin | 0.15 |
| Digitoxigenin | 1.01 |
| Ouabain | 0.06 |

METHOD FOR REMOVING UNDIFFERENTIATED PLURIPOTENT STEM CELLS

RELATED APPLICATIONS

This application is the National Phase of PCT International Application No. PCT/US2018/036213, filed on Jun. 6, 2018, which claims priority under 35 U.S.C. 119 (e) to U.S. Provisional Application No. 62/516,437, filed on Jun. 7, 2017, all of which are hereby expressly incorporated by reference into the present application.

TECHNOLOGY FIELD

The present invention relates to a method for removing undifferentiated pluripotent stem cells. In particular, the present invention relates to a method for removing oncogenic undifferentiated pluripotent stem cells by using cardiac glycosides (CGs). The present invention also relates to a method for preparing differentiated cells in which undifferentiated pluripotent stem cells have been removed and a method for cell therapy by using such differentiated cells.

BACKGROUND OF THE INVENTION

Human embryonic stem cells (hESCs) and induced pluripotent stem cells (iPSCs) are human pluripotent stem cells (hPSCs) that have unique self-renewal (ability to replicate almost indefinitely) and pluripotency (ability to differentiate into all cell types of the human body except for placental cells) properties. These abilities make hPSCs promising resources for regeneration therapy[1]. However, substantial challenges remain to be overcome before applying hPSCs to cell therapy. An important safety concern of hPSCs is their tumorigenic risk because these cells can form teratomas after in vivo injections at ectopic sites[2,3]. Thousands of undifferentiated hPSCs residing in millions of differentiated cells are sufficient to induce teratomas in a mouse model[4]. Thus, it is critical to remove all or most of the residue-undifferentiated hPSCs that have teratoma potential before clinical applications using hPSC-derived cells.

There are several strategies to selectively remove hPSCs. These methods include the use of cytotoxic antibodies[5,6], specific antibody cell sorting[7-9], genetic manipulations[10-12], and pharmacological approaches[13-16]. However, each method has certain disadvantages, such as a high cost (cytotoxic antibodies and specific antibody cell sorting), variation among different lots (cytotoxic antibodies and specific antibody cell sorting)[17,18], non-specific binding (cytotoxic antibodies)[18-20], requirement of genetic manipulation and stable integration of toxic genes (genetic manipulation), and time-consuming procedures (genetic manipulation, specific antibody cell sorting and cytotoxic antibodies). Although many studies have attempted to prevent or block teratoma formation in residual hPSCs, a clinically applicable strategy to eliminate teratoma formation remains to be developed[2,21].

In contrast, small molecule approaches have several advantages as follows: these approaches are robust, efficient, fast, simple, and inexpensive, and there is no need to insert genes into cells. Certain small molecules have been shown to inhibit teratoma formation in hPSCs. The inhibitor of stearoyl-CoA desaturase PluriSin #1 prevented teratoma formation[15]. Stearoyl-CoA desaturase is a key enzyme in the biosynthesis of mono-saturated fatty acids and is required for hPSC survival[15]. The N-benzylnonanamide JC011 induced ER stress through the PERK/AT4/DDIT3 pathway[22]. Chemical inhibitors of survivin, such as quercetin and YM155, induced selective cell death and efficiently inhibited teratoma formation[14]. However, neither of these drugs is well defined or approved by the FDA.

Cardiac glycosides (CGs) (also named cardiotonic steroids, CSs) belong to a large family of compounds that can be derived from nature products. Although these compounds have diverse structures, they share a common structural motif. These compounds are specific inhibitors of the transmembrane sodium pump ($Na^+/K^+$-ATPase). CGs inhibit the $Na^+/K^+$-ATPase and then increase the intracellular concentrations of calcium ions 23. These compounds act as positive inotropic agents, and members of this group have been used in the treatment of heart failure for more than 200 years. One member of this family, digoxin, is still in clinical use[24]. Furthermore, CGs are currently considered to have a potential therapeutic role in cancer therapy[25]. Several studies have reported that CGs play important roles in inducing cell death in several cancer cells[23]. Cancer cells show more susceptibility than cells in normal tissues. The molecular mechanism may be the overexpression of specific alpha subunits of $Na^+/K^+$-ATPase in cancerous cells[26]. These studies indicate that CGs are selective according to the cell type and distinguish between normal cells and transformed cells.

Although cardiac glycosides act as multiple signal transducers, no studies have investigated whether these drugs can eliminate undifferentiated PSCs while sparing their progeny or differentiated cells.

SUMMARY OF THE INVENTION

In this invention, it is unexpectedly found that cardiac glycosides (CGs) can specifically induce cell death in human embryonic stem cells (hESCs) but not in differentiated cells or hESC-derived mesenchymal stem cells (MSCs). It is also found that cardiac glycosides (CGs) significantly inhibits tumor formation activity of hESCs but do not affect the pluripotent ability of theses hESCs.

Therefore, in one aspect, the present invention provides a method for removing undifferentiated pluripotent stem cells from a sample comprising said cells, the method comprising exposing said samples to an effective amount of a cardiac glycoside.

In some embodiments, the cardiac glycoside as used herein is a compound of Formula (I) or a pharmaceutical acceptable salt thereof,

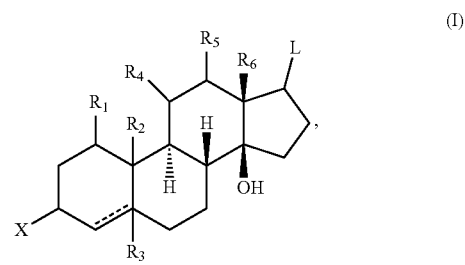

wherein L is a lactone group;
$R_1$, $R_4$ and $R_5$ are independently H or OH;
$R_2$ is $CH_3$ or $CH_2OH$;
$R_3$ is H or OH when the dotted line is absent or R3 is absent when the dotted line forms a double bond;
$R_4$ is H or OH;
$R_5$ is H or OH;
$R_6$ is $CH_3$; and
X is —OH or a glycoside of 1 to 6 sugar residues, each unsubstituted or substituted.

In some embodiments, the lactone group is a unsaturated, five- or six-membered lactone ring.

In some embodiments, the sugar residues are selected from the group consisting of rhamnose, glucose, digitoxose, digitalose, digginose, sarmentose, vallarose, and fructose.

In some embodiments, the sugar residues are unsubstituted or substituted with an acyl group, an amino group, a halogen group and/or an acylamido group.

In particular embodiments, the compound of Formula (I) is selected from the group consisting of:

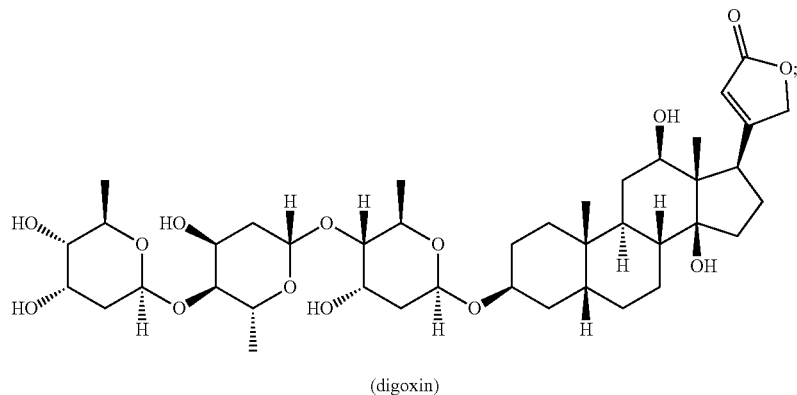

(digoxin) (I)-1

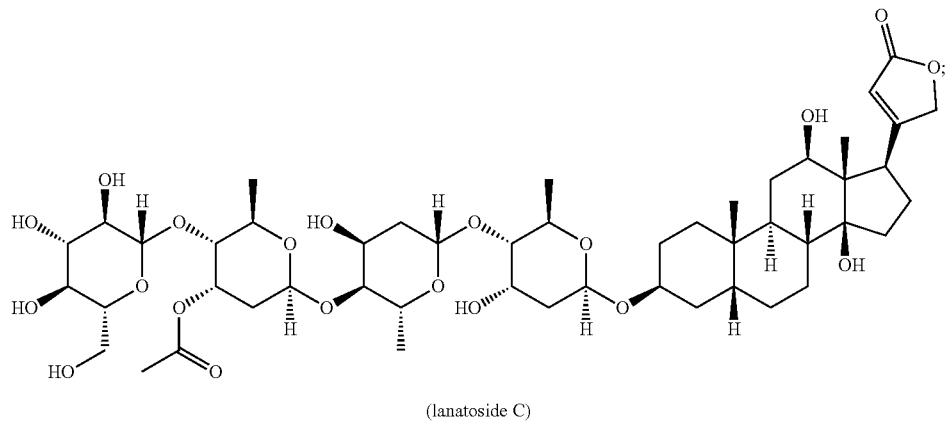

(lanatoside C) (I)-2

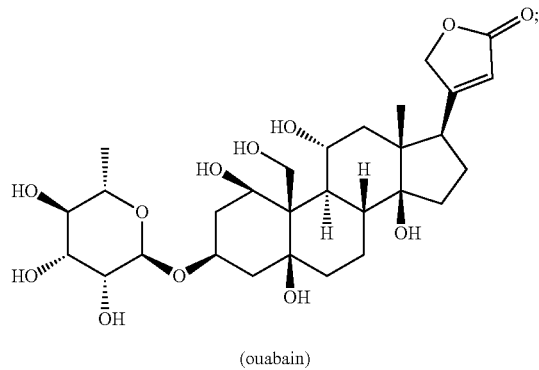

(ouabain) (I)-3

-continued

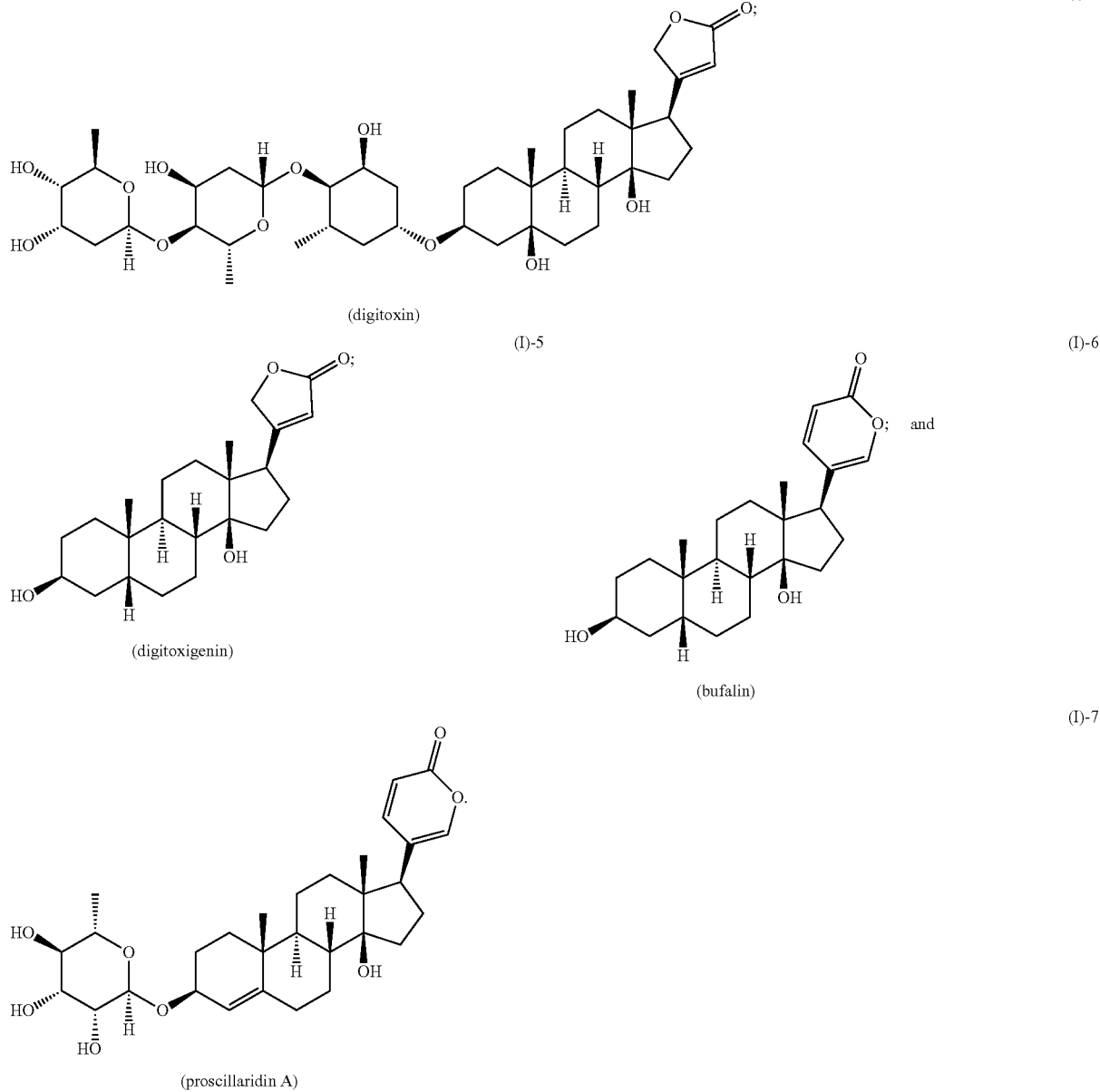

In some embodiments, the undifferentiated pluripotent stem cells are selected from the group consisting of embryonic stem cells (ESCs) and induced pluripotent stem cells (IPSC).

In some embodiments, the undifferentiated pluripotent stem cells express a cell marker selected from the group consisting of $Na^+/K^+$-ATPase, Nanog, Oct4, Sox2, SSEA3, SSEA4, TRA-1-60, TRA-1-81 and a combination thereof.

In some embodiments, the sample further comprises differentiated cells.

In some embodiments, the method further comprises culturing the differentiated cells to provide a cell population of said differentiated cells.

In some embodiments, the differentiated cells are mesenchymal stem cells (MSCs). In particular, the MSCs express a cell marker selected from the group consisting of consisting of $CD44^+$, $CD73^+$, $CD90^+$, $CD105^+$ and a combination thereof, and typically are $CD45^-$, $CD34^-$, $CD11b^-$, $CD19^-$, and/or $HLA-DR^-$.

In some embodiments, the differentiated cells are selected from the group consisting of osteoblasts, adipocytes, chondrocytes, endothelial cells, neuron cells and hepatocytes.

In another aspect, the present invention provides a method for preparing differentiated cells, comprising
(i) subjecting undifferentiated pluripotent stem cells to a condition suitable for differentiation to produce a cell population that comprises differentiated cells and undifferentiated pluripotent stem cells;
(ii) removing the undifferentiated pluripotent stem cells by exposing the cell population to an effective amount of a cardiac glycoside; and
(iii) optionally culturing the remaining differentiated cells.

In some embodiments, the cardiac glycoside as used herein is a compound of Formula (I) or a pharmaceutical acceptable salt thereof as described herein.

In a further aspect, the present invention provides a method for treating a subject in need of cell therapy, comprising administrating to the subject a cell population comprising differentiated cells wherein the cell population prior to administration to the subject has been exposed with a cardiac glycoside, whereby undifferentiated cells present in the cell population, if any, are removed. In some embodiments, the cardiac glycoside as used herein is a compound of Formula (I) or a pharmaceutical acceptable salt thereof as described herein.

Also provided herein is use of a cardiac glycoside for manufacturing a composition for inducing cell death of undifferentiated pluripotent stem cells and/or removing undifferentiated pluripotent stem cells from differentiated cells. Further provided is a composition for cell therapy comprising a cardiac glycoside and a cell population that comprises differentiated cells. In some embodiments, the cardiac glycoside as used herein is a compound of Formula (I) or a pharmaceutical acceptable salt thereof as described herein.

Further provided is a method for treating teratoma in a subject in need, comprising administering to the subject an effective amount of a cardiac glycoside.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1A shows protein expression levels of the $Na^+/K^+$-ATPase alpha1 and alpha2 subunit in hESCs and hMSCs detected by western blotting.

FIG. 1B and FIG. 1D shows cell colony and morphology of hESCs and hMSCs under bright field. hESCs and MSCs treated with DMSO solvent control, 2.5 μM digoxin or 2.5 μM lanatoside C (for 12 hours and 24 hours). Scale bar: 500 μm. FIG. 1C and FIG. 1E shows LDH release measured in hESCs and hMSCs to investigate the cytotoxic effect in 96-well culture dishes. DMSO, 2.5 μM digoxin, or 2.5 μM lanatoside C was used to treat the hESCs of hMSCs for 24 hours, and the supernatant was harvested for the LDH detection. The samples were normalized to the DMSO-treated hESCs. *P<0.001; P<0.01; n.s. not significant. Data are shown as the mean SD.

FIG. 2A shows hESCs treated with DMSO, 1.25 μM digoxin, or 2.5 μM lanatoside C for 24 hour. The bar graph represents the statistical results of the Flow cytometry data. *P<0.05; Data are shown as the mean SD. FIG. 2B shows hMSCs treated with DMSO, 2.5 μM digoxin, or 2.5 μM lanatoside C for 24 hours. Cells were stained with PI and Annexin V and subjected to flow cytometry analysis. Live cells are represented by $PI^-$/Annexin $V^-$; dead cells are represented by $PI/Annexin V^+$, $PI^+/Annexin$, and $PI^+/Annexin^+$. The bar graph represents the statistical results of the FASC data. n.s. not significant. Data are shown as the mean SD. FIG. 2C and FIG. 2D show protein levels of the cleaved form of the apoptotic markers and pluripotent stem cell markers detected by western blotting. hESCs and hMSCs were treated with DMSO, 2.5 μM digoxin or 2.5 μM lanatoside C for 12 hours. Cells were harvested, and the cleaved and uncleaved forms of PARP, caspase7, and caspase3 were detected. For the detection of the pluripotent stem cell markers, the cells were harvested, and Nanog and Oct4 were detected.

FIG. 3A shows that osteogenic differentiation. Mineralization was stained with Alizarin Red S, and the quantification was performed at O.D 570 nm. FIG. 3B shows adipogenic differentiation. Lipid drop was stained with oil red, and quantification was performed at O.D 510 nm. FIG. 3C shows chondrogenic differentiation. Glycosaminoglycan was stained with Alcian blue, and quantification was performed at O.D 650 nm. Scale bar: 500 μm. n.s. not significant. Data are shown as the mean SD.

FIG. 4A show cell morphology of H9 hESC-MSCs under bright field. hESC-MSCs were treated with DMSO solvent control, 2.5 μM digoxin or 2.5 μM lanatoside C for 12 hours and 24 hours respectively. Scale bar: 500 μm. FIG. 4B shows LDH release in hESC-MSCs measured to investigate the cytotoxicity effect in 96-well culture plates. Cells were treated with DMSO or the drugs for 24 hours, and then, the supernatant was harvested for the LDH detection. The samples were normalized against the DMSO-treated hESCs. FIG. 4C shows flow cytometry for the cell death analysis. hESC-MSCs were treated with DMSO, 2.5 μM digoxin or 2.5 μM lanatoside C for 24 hours. Cells were stained with PI and Annexin V, and the cells were analyzed by flow cytometry. The bar graph represents the statistical results of the Flow cytometry data. n.s. not significant. Data are shown as the mean SD. FIG. 4D shows hESCs and hESC-MSCs treated with DMSO, 2.5 μM digoxin or 2.5 μM lanatoside C for 12 hours. Cells were harvested, and the cleaved and uncleaved forms of PARP, caspase3 and caspase7 were detected by western blotting. FIG. 4E shows protein expression levels of the $Na^+/K^+$-ATPase alpha1 and alpha2 subunits in the hESCs and hESC-MSCs detected by western blotting.

FIG. 5A shows the picture. FIG. 5B shows quantification of the teratoma weight. Dot: DMSO; Square: digoxin; Triangle: lanatoside C. ****P<0.0001. Data are shown as the mean SD. FIG. 5C shows these images of a DMSO-treated hESC-derived teratoma. These teratoma paraffin sections were stained with H&E staining (top panel) and IHC staining of three lineage markers (bottom panel). AFP (alpha-fetoprotein): endoderm marker. SMA (smooth muscle actin): mesoderm marker. Tuj1 (beta-III tubulin): ectoderm marker. Scale bar: 50 µm.

FIG. 6A shows cell colony and morphology of HUES6 under bright field. S6 hESCs were treated with DMSO, 2.5 µM digoxin, or 2.5 µM lanatoside C for 12 hours and 24 hours. Cells became round and died. FIG. 6B shows S6 hESCs treated with DMSO, 2.5 µM digoxin, or 2.5 µM lanatoside C for 24 hours. The culture supernatant was harvested for the LDH release detection. ***P<0.001. Data are shown as the mean SD.

FIG. 8A to FIG. 8D include charts showing the results of the cytotoxic assay. FIG. 8A shows a schematic diagram of the differentiation process and that MSCs are derived from H9 hESCs. FIG. 8B shows the phenotype of passage 1 hESC-MSCs analyzed and sorted by CD73 and CD105. FIG. 8C shows that general MSC-positive and MSC-negative markers were analyzed in the hESC-MSCs. Positive markers: CD73, CD90, CD44, and CD105; negative markers: CD45, CD34, CD11b, CD19, and HLA-DR. FIG. 8D shows that hESC-MSCs were individually treated with different cardiac glycosides at a final concentration of 2.5 µM for 24 hours and followed by measuring the amount of released LDH in the cytotoxic assay. n.s. not significant. Data are shown as the mean SD.

FIG. 9A shows FASC analysis of the endothelial cell markers CD34 and CD144, which demonstrated over 90% CD34+/CD144+ population in hiPSC-endothelial cells. FIGS. 9B and 9C show the results of the cytotoxicity assay where cells were treated with 2.5 µM of digoxin and 2.5 µM lanatoside C for 24 hours, and the amount of released LDH was measured in the cytotoxic assay. Cardiac glycosides induced cytotoxicity in the undifferentiated hiPSCs but did not affect the survival of hiPSC-endothelial cells. FIG. 9D shows immunofluorescence staining represented the neuron marker TUJ1 in hESC-neuron. Green: TUJ1: DAPI (blue): nucleus. FIG. 9E shows that hESC-neurons were treated with 2.5 µM of digoxin and 2.5 µM lanatoside C for 24 hours, and cytotoxicity was not induced according to the measured released LDH. FIG. 9F shows immunofluorescence staining represented the hepatocyte marker AFP in the hESC-hepatocyte endoderm. Green: alpha-fetoprotein; DAPI (blue): nucleus. FIG. 9G shows that hESC-hepatocyte endoderm cells were treated with 2.5 µM digoxin and 2.5 µM lanatoside C for 24 hours, and cytotoxicity was slightly induced, as measured by the released LDH. Scale bar: 200 µm. **P<0.01; *P<0.05; n.s. not significant. Data are shown as the mean SD.

FIG. 11A shows that GFP-overexpressing hBMMSCs were injected under the kidney capsule, and hBMMSCs were stained with the GFP antibody to demonstrate that cells remain in the NSG mice. FIG. 11B shows that Left panel: teratoma sections were obtained from mixtures of undifferentiated hESCs and GFP-overexpressing hBMMSCs that both were treated with DMSO, digoxin or lanatoside C under the kidney capsule in NSG mice; and right panel: tumor area of kidney tissue was quantified using image scope software. (n=3) Scale bar: 2 mm. FIG. 11C shows that teratoma sections were stained with the GFP antibody (top panel) and H&E (bottom panel), which showed that the drug-treated hBMMSCs remained in the engraft site. Scale bar: 50 m.

DETAILED DESCRIPTION OF THE INVENTION

Figure 1A:
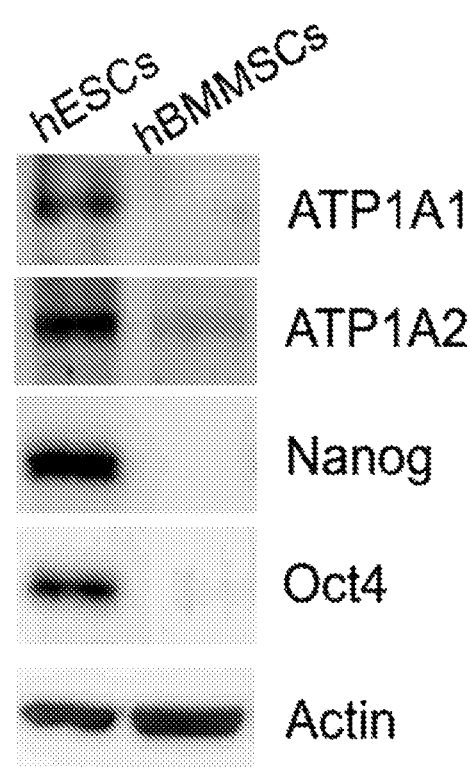
FIG. 1A to FIG. 1E include charts showing that cardiac glycosides induced cytotoxic effect in hESCs but not in hMSCs.

Unless defined otherwise, all technical and scientific terms used herein have the same meaning as commonly understood by a person skilled in the art to which this invention belongs.

1. Definitions

As used herein, the singular forms "a", "an", and "the" include plural referents unless the context clearly dictates otherwise. Thus, for example, reference to "a component" includes a plurality of such components and equivalents thereof known to those skilled in the art.

The term "comprise" or "comprising" is generally used in the sense of include/including which means permitting the presence of one or more features, ingredients or components. The term "comprise" or "comprising" encompasses the term "consists" or "consisting of."

As used herein, the term "undifferentiated pluripotent stem cells" refer to cells that are capable of self-renewal and pluripotent. The term "pluripotent" means the ability of a cell to differentiate into all cell lineages except placenta. Specifically, pluripotent cells include those that can differentiate into the three main germ layers: endoderm, ectoderm, and mesoderm. In general, undifferentiated pluripotent stem cells are embryonic stem cells (ESCs), which may be derived from embryonic sources e.g. pre-embryonic, embryonic or fetal tissues at any time after fertilization. Undifferentiated pluripotent stem cells can also include induced pluripotent stem cells (IPSCs) that are artificially derived from non-pluripotent cells (e.g., somatic cells) by insertion of one or more specific genes or by stimulation with chemicals. The induced pluripotent stem cells are considered the same as pluripotent stem cells (e.g., embryonic stem cells) in that the induced pluripotent stem cells have the two unique characteristics i.e. self-renewal capacity and pluripotency as well. ESCs or IPSCs are capable of forming teratoma. ESCs or IPSCs are further known to express certain cell markers such as $Na^+/K^+$-ATPase, Nanog, Oct4, Sox2, SSEA3, SSEA4, TRA-1-60, TRA-1-81, alkaline phosphatase As used herein, "mesenchymal stromal/stem cells (MSCs)" can self-renew and are multipotent. The term "multipotency" herein refers to a stem cell that has the ability to differentiate into more than one cell types. Multipotent stem cells cannot give rise to any type of mature cells in the body; they are restricted to a limited range of cell types. For example, MSCs can differentiate into osteoblasts, adipocytes, chondrocytes, neurons, p islet cells, intestine cells. MSCs can be obtained from various sources, such as bone marrow, adipose or dental tissues and then cultured for expansion. MSCs can also be derived from ESCs or IPSCs. However, unlike ESCs or IPSCs which are oncogenic, MSCs do not have oncogenic ability and therefore are considered to have greater biosafety. Specifically, MSCs are known to express certain cell markers such as $CD44^+$, $CD73^+$, $CD90^+$, $CD105^+$ but are $CD45^-$, $CD34^-$, $CD11b^-$, $CD19^-$, and/or $HLA-DR^-$.

As used herein, the term "differentiation" refers to a process for differentiating pluripotent stem cells into progeny that are enriched for cells of a particular form or function. Differentiation is a relative process. For example, MSCs are relatively differentiated, compared to ESCs, but still have the ability to differentiate into multiple cell types. Mature somatic cells e.g. osteoblasts (bone), chondrocytes (cartilage), adipocytes (fat), hepatocytes (liver) can be terminally differentiated that already lose the ability to differentiate into different cell types. Therefore, the term "differentiated cells" can refer to relatively differentiated cells e.g. MSCs or terminally differentiated cell e.g. mature somatic cells.

As used herein, the term "remove" or "eliminate" when used with respect to undifferentiated pluripotent stem cells, refers to isolation or separation of such cells from other components in the original sample or from components in the sample that are remaining after one or more steps of processing. The other components for example can include other cells, particularly differentiated cells. The removal or elimination of a target cells may include kill, suppress or deplete the target cells in the samples by applying the compound as used herein, for example, such that other components such as differentiated cells are enriched in the sample. Killing a target cell can include causing apoptosis or cytotoxicity to the cells. Suppressing or depleting a target cell may include a decrease in the number, proportion, proliferation or activity (pluripotent ability or tumor formation activity) by a measurable amount. The removal can be partial or complete. As used herein, a sample or a culture that are substantially free of undifferentiated pluripotent stem cells, for example, can contain less than about 10%, about 5%, less than about 4%, less than about 3%, less than about 2%, less than about 1%, or undetectable undifferentiated pluripotent stem cells.

As used herein, the term "culture" refers to a group of cells incubated with a medium. The cells can be passaged. A cell culture can be primary culture which has not been passaged after being isolated from the animal tissue, or can be passaged multiple times (subculture one or more times).

The term "about" as used herein means plus or minus 5% of the numerical value of the number with which it is being used.

As used here, the term "subject" as used herein includes human and non-human animals such as companion animals (such as dogs, cats and the like), farm animals (such as cows, sheep, pigs, horses and the like), or laboratory animals (such as rats, mice, guinea pigs and the like).

As used herein, the term "treating" as used herein refers to the application or administration of a composition including one or more active agents to a subject afflicted with a disorder, a symptom or conditions of the disorder, or a progression of the disorder, with the purpose to cure, heal, alleviate, relieve, alter, remedy, ameliorate, improve, or affect the disorder, the symptoms or conditions of the disorder, the disabilities induced by the disorder, or the progression of the disorder.

As used herein, the term "effective amount" used herein refers to the amount of an active ingredient to confer a biological effect in a treated cell or subject. The effective amount may change depending on various reasons, such as treatment route and frequency, body weight and species of the cells or individuals receiving said active ingredient.

As used herein, a "lactone" group is a cyclic ester. Specifically, a lactone can be represented by a formula of

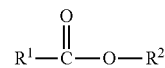

where $R^1$ and $R^2$, taken together, with the carbon and oxygen atoms to which they are attached form an optionally substituted cyclic group which can be saturated, unsaturated or aromatic. $R^1$ and $R^2$ are independently hydrogen or optionally substituted hydrocarbon moiety. The most stable structure for lactones are the 5-membered γ-lactones and 6-membered S-lactones.

"Hydrocarbon" refers to an organic compound consisting of hydrogen and carbon, which can be straight, branched, or cyclic and may include an alkane, an alkene, an alkyne, an arene, or a combination thereof.

The term "glycoside" refers to a compound in which a sugar group or a sugar residue is bound to a non-carbohydrate moiety. Typically the sugar group (glycone) is bonded through its anomeric carbon to another group (aglycone) via a glycosidic bond that has an oxygen, nitrogen or sulfur atom as a linker.

As used herein, a sugar group or a sugar residue can be a simple sugar, an amino sugar, a deoxy sugar, a sugar acid, or a sugar alcohol.

As used herein, the term "optionally substituted" means the group to which this term refers to may be unsubstituted or may be substituted by one or more substituents. Examples of the substituent can include an alkyl group, an alkoxy group, a hydroxy group, an acyl group, a halogen group and/or an acylamido group. Examples of the alkyl group include C1-6 alkyl groups, such as a methyl group, an ethyl group, a n-propyl group, an i-propyl group, a n-butyl group, a s-butyl group, an i-butyl group, a t-butyl group, a n-pentyl group, and a n-hexyl group. Examples of the alkoxy group include C1-6 alkoxy groups, such as a methoxy group, an ethoxy group, a n-propoxy group, an i-propoxy group, a n-butoxy group, a s-butoxy group, an i-butoxy group, and a t-butoxy group. Examples of an acyl group include formyl group, acetyl group, propionyl group, butyryl group, isobutyryl group, valeryl group, isovaleryl group, hexanoyl group, octanoyl group, decanoyl group, lauroyl group, and benzoyl group. Examples of a halogen atom include fluorine atom, chlorine atom, bromine atom, and iodine atom.

As used herein, the term "pharmaceutically acceptable salt" includes acid addition salts. "Pharmaceutically acceptable acid addition salts" refer to those salts which retain the biological effectiveness and properties of the free bases, which are formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethanesulfonic acid, p-toluenesulfonic acid, salicylic acid, trifluoroacetic acid and the like.

2. Compounds

According to the present invention, the active compound as used herein is a cardiac glycoside.

As used herein, a cardiac glycoside is an inhibitor of cell membrane $Na^+/K^+$ ATPase (ATP phosphohydrolase). In particular, cardiac glycosides comprise a steroid core with either a pyrone or butyrolactone substituent at C17 (the "pyrone form" and "butyrolactone form"), and typically be glycosylated at C3. Most cardiac glycosides include one to four sugars attached to the 3β-OH group.

In some embodiments, a cardiac glycoside is a compound represented by Formula (I)

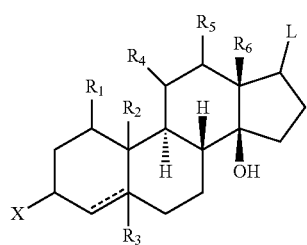

(I)

and a pharmaceutical acceptable salt thereof,
wherein L is a lactone group;
$R_1$, $R_4$ and $R_5$ are independently H or OH;
$R_2$ is $CH_3$ or $CH_2OH$;
$R_3$ is H or OH when the dotted line is absent or $R_3$ is absent when the dotted line forms a double bond;
$R_4$ is H or OH;
$R_5$ is H or OH;
$R_6$ is $CH_3$; and
X is —OH or a glycoside of 1 to 6 sugar residues, each unsubstituted or substituted.

In some embodiments, the lactone group is a unsaturated, five- or six-membered lactone ring In some embodiments, the sugar residues are selected from the group consisting of rhamnose, glucose, digitoxose, digitalose, digginose, sarmentose, vallarose, and fructose.

In some embodiments, X is a glycoside of 1, 2, 3, 4, 5 or 6 sugar residues. In some embodiments, X is a glycoside of two digitoxose, one acetyldigitoxose and one glucose; or X is a glycoside of three digitoxoses; or X is a glycoside of rhamnose.

In some embodiments, the sugar residues are unsubstituted or substituted with an acyl group, an amino group, an acetyl group, a halogen group and/or an acylamido group.

A large number of cardiac glycosides are known in the art. Exemplary cardiac glycoside include, but are not limited to, digoxin, lanatoside C, ouabain, digitoxin, digitoxigenin, bufalin, proscillaridin A, Oleandrin, neriin, neriantin, Odoroside A and B, Ouabain (G-strophantin), cymarin, sarmentocymarin, periplocymarin, K-strophantin, Ouabain, Thevetin, cerberin, peruvoside, Thevetosin, thevetin A, Cerberin, Tanghinin, deacetyltanghinin, cerberin, Echujin, hongheloside G, Periplocin, Strophantidin, strophantidol, nigrescin, Uzarin, Calotropin, Cheiroside A, cheirotoxin, Eounoside, euobioside, euomonoside, Lancetoxin A and B, Kalanchoside, Bryotoxin A-C, Bryotoxin C, bryophyllin B, Cotiledoside, Tyledoside A-D, F and G, Orbicuside A-C, Alloglaucotoxin, corotoxin, coroglaucin, glaucorin, Scillirosidin derivatives, Bovogenin A derivatives, Scillarene A and B, scilliroside, scillarenia, scilliacinoside, scilliglaucoside, scilliglaucosidin, scilliphaeosidin, scilliphaeoside, scillirosidin, scillirubrosidin, scillirubroside, proscillaridin A, Rubelin, Convalloside, convallatoxin, Bovoside A, glucobovoside A, bovoruboside, Antiarin a, Helleborein, helleborin, hellebrin, Adonidin, adonin, cymarin, adonitoxin, Thesiuside, Digitoxin, gitoxin, gitalin, digoxin, F-gitonin, digitonin, lanatoside A-C, Bufotalin, bufotalinin, bufotalidin, Gamabufagin, Cinobufagin, Marinobufagin, Arenobufagin, Regularobufagin, Vallicepobufagin, Quercicobufagin, Viridibufagin, Pseudobufotalin, calotropin, calactinu, scharin, voruscharin, 2"-oxovoruscharin, 16oxovoruscharin, inubufotalin, Vallicepobufagin, Quercicobuy-5α-4,5-dihydro-scillirosidin, 165α-4,5-dihydro-scillirosidin, Vallicepobufagin, Quercicobufagin,oside A-C, hellebrin, Adonidin, adonin, cymarin, adonitoxin, Thesiusidein, scilliphaeoside, schaeosidine and 12β-hydroxy-desacetyl-scillirosidine.

In some examples, the compound is selected from the group consisting of:

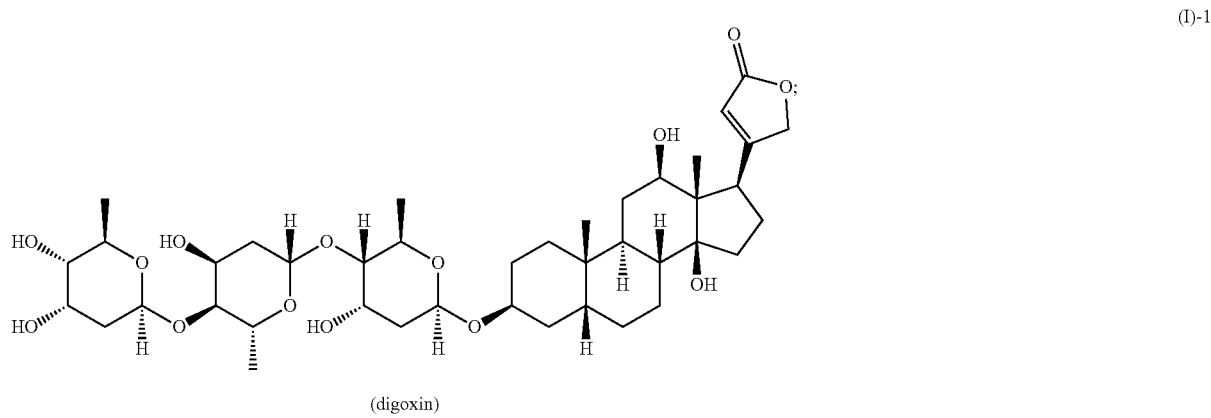

(I)-1

(digoxin)

-continued
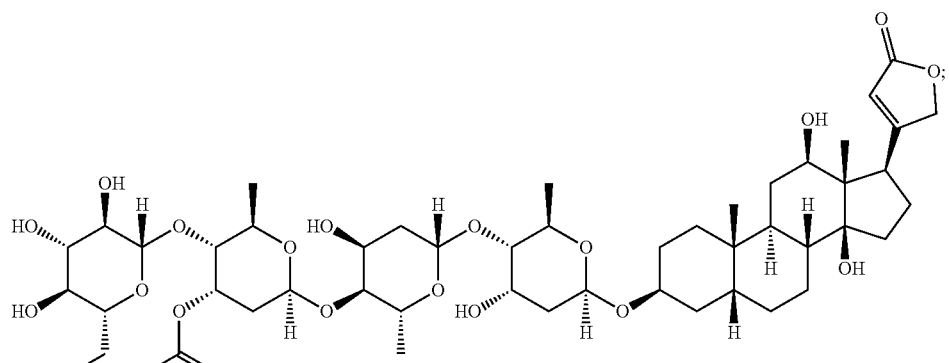
(lanatoside C)
(I)-2
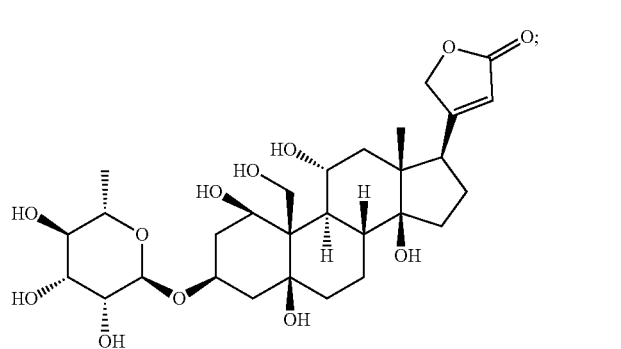
(ouabain)
(I)-3
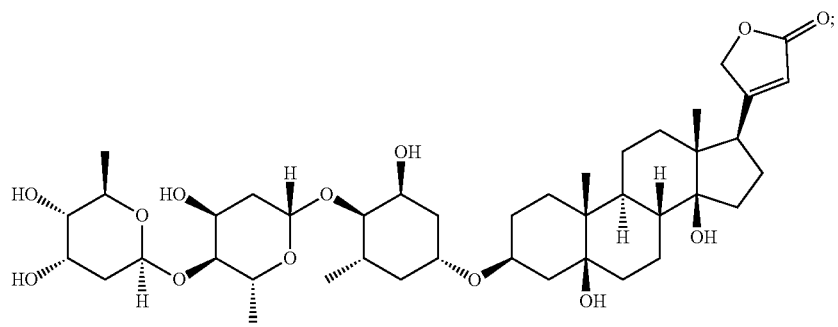
(digitoxin)
(I)-4
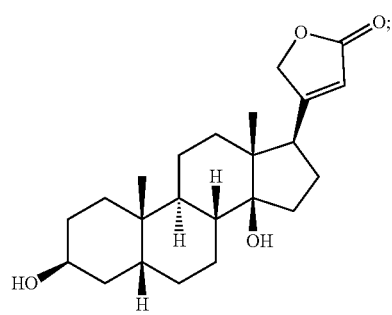
(digitoxigenin)
(I)-5
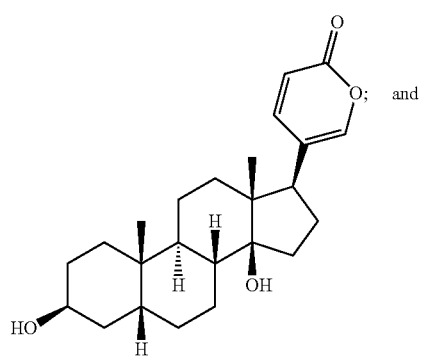
(bufalin)
(I)-6 and

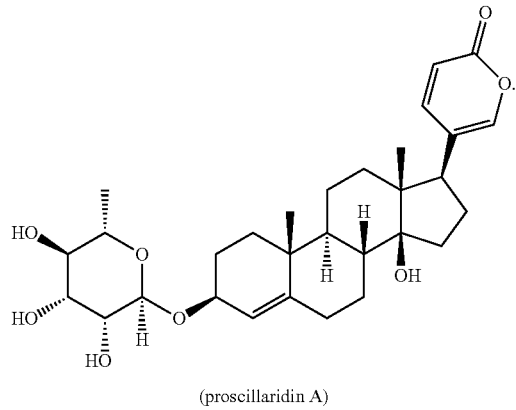

(proscillaridin A)

The compound of the present invention may be prepared by conventional processes or available commercially.

3. Use of Active Compounds

According to the present invention, a cardiac glycoside can be used to induce cell death of undifferentiated pluripotent stem cells and therefore can selectively remove undifferentiated pluripotent stem cells from differentiated cells.

In particular, the present invention provides a method for removing undifferentiated pluripotent stem cells from a sample comprising said cells, comprising exposing said sample to an effective amount of a cardiac glycoside.

In some embodiments, the sample is a cell sample that comprises cells in culture (in vitro) that is to be transferred to a patient in need of cell therapy.

In particular, the present invention also provides a method for preparing differentiated cells, comprising
  (i) subjecting undifferentiated pluripotent stem cells to a condition suitable for differentiation to produce a cell population that comprises differentiated cells and undifferentiated pluripotent stem cells;
  (ii) removing the undifferentiated pluripotent stem cells by exposing the cell population to an effective amount of a cardiac glycoside; and
  (iii) optionally culturing the remaining differentiated cells.

In some embodiments, undifferentiated pluripotent stem cells are selected from the group consisting of embryonic stem cells (ESCs) and induced pluripotent stem cells (IPSCs). Preferably, the pluripotent stem cells are sourced from humans. Human ESCs can be obtained from human blastocyst cells using the techniques known in the art. Hunan IPSCs can be prepared by isolating and culturing suitable somatic donor cells, for example, human fibroblasts, and subjected to genetic engineering using techniques known in the art.

In some embodiments, undifferentiated pluripotent stem cells are cultured in a culture medium under condition which allows a proportion of the undifferentiated pluripotent stem cells to differentiate into differentiated cells of interest, then an effective amount of a cardiac glycoside is added to the culture medium to cause cell death of residual undifferentiated pluripotent stem cells, and optionally the remaining differentiated cells are further cultured for expansion which are then administered to a subject in need of cell therapy.

In some embodiments, the culture medium suitable for culturing undifferentiated pluripotent stem cells and/or differentiated cells according to the present invention are available in this art, such as DMEM, MEM, or IMEM medium with 10% Fetal bovine serum. The culture can be carried out at in a normal condition, for example, 37° C. under 1-5% $CO_2$. Typically, a suitable amount of a cardiac glycoside is added to the culture medium to achieve a concentration from 0.1 µM to 100 µM and then the cell culture in the presence of the cardiac glycoside is performed for at least 3 hours, at least 6 hours, preferably 12 hours, more preferably 24 hours, to cause cell death of residual undifferentiated pluripotent stem cells. Differentiation may be promoted by adding a medium component which promotes differentiation towards the desired cell lineage.

By treatment with a cardiac glycoside, residual undifferentiated pluripotent stem cells can be selectively killed and removed from their differentiated progenies so that a sample comprising the differentiated progenies after removing residual undifferentiated pluripotent stem cells can be applied in cell therapy with reduced tumorigenic risk. Particularly, alive undifferentiated pluripotent stem cells after treatment with a cardiac glycoside is in an amount less than that of a control (e.g. the same cells without such treatment) by about 10%, 20%, 30%, 40%, 50%, 60%, 70%, 80% or 90%. More particularly, the removal is complete; namely, undifferentiated pluripotent stem cells after such treatment are completely killed and no residual undifferentiated pluripotent stem cells are detectable.

Therefore, the present invention further provides a method for treating a subject in need of cell therapy, comprising administrating to the subject an effective amount of a cell population comprising differentiated cells wherein the cell population prior to administration to the subject has been exposed with a cardiac glycoside whereby undifferentiated pluripotent cells present in the cell population, if any, are substantially removed. Typically, the cell population is further replaced with fresh medium that is free of the cardiac glycoside so that the cell population prior to administration to the subject does not contain the cardiac glycoside.

Also provided is a composition comprising a cardiac glycoside and a cell population comprising differentiated cells. Specifically, the cell population prior to administration to the subject has been exposed with a cardiac glycoside whereby undifferentiated cells present in the cell population, if any, are substantially removed.

Typically, a composition is formulated with a pharmaceutically acceptable carrier for the purpose of delivery and efficacy. As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered as needed.

In some embodiments, a subject who in in need of cell therapy has a disease or condition including but not limited to macular Degeneration, graft-versus-host disease, heart diseases (e.g. peripheral arterial disease, ischemia, stroke, myocardial infraction), acute lung injury (ALI), Crohn's disease, type 1 diabetes mellitus, multiple sclerosis, neurological diseases, osteogenesis imperfecta, ischemia, fibrosis, and inherited diseases such as Hurler's syndrome, anti-inflammation (immunomodulatory capacity), cardiovascular disease, neurodegenerative disorders, tissue engineering and the like. Treatment may use the cells to construct new tissue (with or without biomaterials), according to any method known in the art. The cells may be injected or transplanted to the site of tissue damage so that they will produce new tissue in vivo. For example, MSCs may be applicable in cartilage and bone regeneration for the treatments of arthritis, lower back pain (LBP), cartilage degeneration, bone fracture, or osteoporosis. In addition, since MSCs can differentiate into fat and cartilage, MSCs may also be applicable in plastic surgery such as autologous fat transplantation and cartilage grafting in nasal augmentation.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

Examples

An important safety concern in the use of human pluripotent stem cells (hPSCs) is tumorigenic risk because these cells can form teratomas after an in vivo injection at ectopic sites. Several thousands of undifferentiated hPSCs are sufficient to induce teratomas in a mouse model. Thus, it is critical to remove all residue-undifferentiated hPSCs that have teratoma potential before the clinical application of hPSC-derived cells. In this study, our data demonstrated the cytotoxic effect of cardiac glycosides, such as digoxin, lanatoside C, bufalin, and proscillaridin A, digitoxin, digitoxigenin, ouabain in undifferentiated human embryonic stem cells (hESCs). This phenomenon was not observed in human bone marrow mesenchymal stem cells (hBMMSCs). Most importantly, digoxin and lanatoside C did not affect the stem cells' differentiation ability. Consistently, the viability of the hESC-derived MSCs, neurons, and endothelium cells, hepatocyte endoderm was not or slightly affected by the digoxin and lanatoside C treatment. Furthermore, the in vivo experiments demonstrated that digoxin and lanatoside C prevented teratoma formation. According to the present invention, it is the first time to describe the cytotoxicity and tumor prevention effects of cardiac glycosides in hESCs. Digoxin and lanatoside C are also the first FDA-approved drugs that demonstrated cytotoxicity in undifferentiated hESCs.

1. Material and Methods

All methods were performed in accordance with the relevant guidelines and regulations. All experiments were approved by Human Subject Research Ethics (AS-IRB02-106069) and Institutional Animal Care & Utilization Committee (IACUC, 14-03-684), Academia Sinica (Taipei, Taiwan). All culture medium and supplements unless otherwise specified, were obtained from ThermoFisher Scientific (Wilmington, DE, USA). All chemicals unless otherwise specified, were brought from Sigma (St. Louis, MO, USA)

1.1 Cell Lines and Culture Conditions

The hESC line H9 was purchased from WiCells (Madison, WI, USA)[27]. Another hESC line, HUES6, was kindly provided by Dr. Douglas A. Melton (Harvard University, Boston, MA, USA)[28]. Cells were maintained on the feeder cells and cultured in Dulbecco's modified Eagle's medium (DMEM)/F12 supplemented with 20% knockout serum replacement, 2 mM L-glutamine, 1% nonessential amino acids, 4 ng/mL human bFGF, and 0.1 mM 2-mercaptoethanol. For the feeder cells culture, C57BL/6 mouse embryonic fibroblasts (MEF) were cultured in the DMEM with 10% FBS and treated cells with 0.01 mg/ml mitomycin C 2-6 hours for inactivation. For the feeder-free culture, hESCs were seeded on the Matrigel Matrix (BD Biosciences, San Jose, CA, USA) coated culture plates and maintained by conditioned medium of MEF (C57BL/6). hBMMSCs were cultured in mesenPRO RS™ kit (Life Technologies, Camarillo, CA, USA). All cells were cultured in a humidified atmosphere containing 5% CO2 at 37° C.

1.2 Lactate Dehydrogenase (LDH) Cytotoxicity Assay

The supernatants of cells treated with digoxin 2.5 M, lanatoside C 2.5 µm, or DMSO solvent control for 24 hours were harvested. The released LDH was measured using CytoTox 96 Non-Cytotoxicity assay according to the manufacture's instruction (Promega, Southampton, UK). The supernatants and reagents were incubated at room temperature for 20 minutes and then the reaction was stopped by Stop Solution. The absorbance at 490 nm was measured using a plate-reading spectrophotometer (Benchmark Plus Microplate Spectrophotometer System, BIO-RAD, CA, USA).

1.3 Western Blot Analysis

RIPA buffer was used to harvest cell lysates (RIPA buffer: NaCl 150 mM, Tris pH 8.0 50 mM, EDTApH 8.0 5 mM, NP-40 1.0%, SDS 0.5%, sodium deoxycholate 0.1%). Western blot analyses were performed as previously described with different types of primary antibodies[29]. The primary antibody includes anti-β-actin (A5441; Sigma), anti-Oct4 (sc-9081; Santa Cruz Biotechnology, Santa Cruz, CA, USA), anti-Nanog (3580; Cell Signaling Technology, Danvers, MA, USA), apoptosis antibody kit (9915; Cell Signaling Technology), ATP1A1 (3010; Cell Signaling Technology), and ATP1A2 (16836-1-AP; Proteintech™) were used. After reaction at 4° C. overnight, the blots were incubated with goat anti-mouse- or goat anti-rabbit antibody conjugated with horseradish peroxidase (Jackson ImmunoResearch Inc). The chemiluminescent substrate (WBKLS0500;

Millipore, Darmstadt, Germany) was used to detect the blots. Fujifilm LAS-4000 (FUJIFILM, Tokyo, Japan) was used to take the images.

1.4 Flow Cytometry

For cell death assay, Propidium iodine/Annexin V assay was performed according to the manufacturer's instruction (Alexa Fluor® 488 Annexin V/Dead Cell Apoptosis Kit; Life Technologies). In brief, live cells were dissociated with trypsin and incubated with Annexin V antibody and PI working solution for 15 minutes. We added 400 μl 1× annexin binding buffer and analyzed the stained cells by FACSCanto™ (Becton Dickinson, Franklin Lakes, NJ, USA). For analyzing the phenotypic signature of MSCs we used a Stemflow™ hMSC analysis kit (BD Biosciences) and FACSCanto™. All flow data was analyzed by FACSDivam software (BD Biosciences) and FlowJo™ (FlowJo, LLC, Ashland, USA).

1.5 hESC-Derive MSCs

According to the report from Dr. Xu and colleagues[30], hESCs were cultured with 10 ng/ml BMP4 and 1 μM of A8301 for 5 days. Next, the cells were passaged on the gelatin-coated plate and the culture medium was switched to MSC culture medium [Minimum Essential Medium Eagle Alpha Modification (αMEM) medium supplemented with 20% fetal bovine serum (FBS), 1-glutamine (Gluta-MAX), 1× nonessential amino acids]. Cells were expanded within passage 5, and CD73$^+$ (11-0793, ThermoFisher Scientific) and CD105$^+$ (12-1057, ThermoFisher Scientific) double positive cells were sorted.

1.6 Cell Sorting hESC-derived MSCs were trypsinized and washed with PBS. Then cells were incubated with anti-human CD73 FITC (ThermoFisher Scientific) and anti-human CD105 PE (ThermoFisher Scientific) for 15 minutes at 4° C. Cells were washed cells with PBS for three times. CD73$^+$/CD105$^+$ cells were sorted with the cell sorter (BD FACSAria II, BD Biosciences). Sorted cells were maintained in MSC culture medium.

1.7 Osteogenic Differentiation and Alizarin Red S Staining

BMMSCs were treated with digoxin (2.5 μM), lanatoside C (2.5 μM), or DMSO solvent control for 24 hours. Drugs were removed, and the cells were washed with PBS and cultured in MSCgo™ Osteogenic Differentiation medium (Biological Industries, Kibbutz Beit-Haemek, Israel)[31]. The media changed twice per week for 14-21 days. Next, the cells were fixed with ice-cold 70% ethanol at −20° C. for 1 hour. After washing with water for three times, the cells were then stained with 40 mM Alizarin Red S (ARS) (pH 4.2) at room temperature for 10 minutes. The cells were then washed with PBS for five times. An Olympus CK-40 microscope was used to take the images. For quantification, the dye was extracted with 10% (w/v) cetylpyridinium chloride (Sigma 0732) in sodium phosphate buffer (pH 7.0) for 15 minutes, and the O.D. at 570 nm was measured.

1.8 Adipogenesis and Oil Red O Assay hBMMSCs were treated with digoxin (2.5 μM), lanatoside C (2.5 μM), or DMSO solvent control for 24 hours. Next, drugs were removed, and the cells were cultured in MSCgo™ Adipogenic Differentiation Medium (Biological Industries). The media was changed every 3-4 days for 8-12 days. After the adipogenic induction, we replaced the MSCgo™ Adipogenic complete medium with MSC maintenance medium for 6-9 days. The cells were carefully fixed with 4% formaldehyde for 1 hour at room temperature, washed with 60% isopropanol, and air-dried. The lipid drops were stained with Oil Red O working solution (30 ml 0.35% oil red solution in isopropanol diluted with 20 ml of distilled water) for 10 minutes. Next, the cells were washed with water 4 times. For quantification, Oil Red O stain was extracted with 100% isopropanol, and the absorbance at 510 nm was detected.

1.9 Chondrogenic Induction and Alcian Blue Assay

BMMSCs were treated with digoxin (2.5 μM), lanatoside C (2.5 μM), or DMSO solvent control for 24 hours. Next, drugs were removed, and 1×10$^5$ cells were seeded in 96-well U-bottom culture plated. After 24 hours, we changed the complete MSCgo™ Chondrogenic medium (Biological Industries) for 21 days. The media were changed every 3-4 days. Next, the pelleted cells were fixed with 4% formaldehyde for 1 hours, washed twice with ddH$_2$O, and stained with a 1% Alcian blue solution in 0.1N HCl for 30 min. For Alcian Blue elution, we added 8 μM Guanidine HCL solution and incubated overnight at RT. The absorbance at 650 nm was detected.

1.10 In Vivo Tumorigenicity Assay and Immunohistochemistry hESCs were treated with digoxin (2.5 M), lanatoside C (2.5 M), or DMSO control for 24 hours. Approximately 10$^6$ treated cells were mixed with 10$^5$ MEFs to promote teratoma formation in 50 μl PBS[32]. The cells mixture and 1× Matrigel Matrix was mixed well and the cells were subcutaneously injected into NOD scid gamma mice (NSG mice) for 8 weeks. After 8 weeks, animals were sacrificed and teratoma was removed, fixed in 10% formalin, embedded in paraffin and stained with hematoxylin and eosin. H&E stain protocol was modified from previous study[33]. For immunohistochemistry, teratoma sections were blocked using 5% milk for 1 hour, and stained with primary antibody at 4° C. overnight, follow by secondary antibody (Dako, Santa Clara, CA, USA) for 1 hour at RT and DAB enhancer (Dako). Primary antibody: anti-human alpha-1-fetoprotein (A0008, Dako) for endoderm lineage; anti-human smooth muscle actin, clone 1A4 (M0851, Dako) for mesoderm lineage; anti-Tuj1 (MAB1637, EMD Millipore, Darmstadt, Germany) for ectoderm.

1.11 Differentiation of hiPSC Cells into Endothelial Cells hiPSC-derived endothelial cells were prepared according in a previous report[34]. The hiPSCs were maintained in mTeSR 1 medium (STEMCELL Technologies, Vancouver, Canada) on VTN-N coated plates (Thermo, Wilmington, DE, USA). First, for the stepwise induction of differentiation, we performed a mesoderm induction of hiPSCs seeded in mesoderm induction medium for 48 hours (basal medium with 10 mM of Y-27632, 3 mM of CHIR99021, and 2 ng/ml of Activin A; basal medium was composed of 12 g/L of DMEM/F-12, 3.56 g/L of HEPES, 1.742 g/L of sodium bicarbonate, 14 μg/L of sodium selenite, 10.7 mg/L of recombinant transferrin, 19.4 mg/L of recombinant insulin, and 64 mg/L of L-Ascorbic acid 2-phosphate sesquimagnesium salt hydrate). Second, for the mesoderm to endothelium transition, mesoderm cells were reseeded in vasculogenic medium (basal medium with 2 mg/ml of PVA plus 20 ng/ml of hVEGF-A) for an additional 72 hours. All differentiated cells were plated on VTN pre-coated culture plate dishes. The endothelial cells were analyzed on day 5 by flow cytometry staining with the CD31 (PECAM1, ThermoFisher Scientific, Wilmington, DE, USA) and CD144 (CDH5, ThermoFisher Scientific) antibodies.

1.12 Differentiation of hESCs into Neurons

The neuron induction protocol is based on a previous study[35]. Briefly, hESCs were detached by a 1 mg/ml collagenase IV treatment for 1 hour and re-suspended in an embryoid body (EB) medium (a bFGF free hESCs culture medium containing 2 μM dorsomorphin and 2 μM A-83-

01b) in non-treated polystyrene plates for 7 days. Then, the EBs were seeded on Matrigel-coated 6-well plates, and the medium was replaced by A neural progenitor cell (NPC) medium consisting of DMEM/F12: Neurobasal=1:1, 1% N2, 1% B27, 1% NEAA, 1% GlutaMax, 2 μg/ml heparin and 2 μM cyclopamine. The attached EBs were cultured for 14 days with the NPC medium, and the medium was changed every other day. The neural progenitor cells were selected mechanically and then re-suspended on 6 well plate coated with ultra-Low Attachment Surface (Cat. No. 3471, Corning, NY) in the NPC medium. For the neuronal differentiation, suspended neural progenitor spheres were treated with Accutase for 10 min and placed onto poly-D-lysine coated coverslips in the neuronal culture medium, which consisted of Neurobasal medium supplemented with 1% GlutaMax, 1% B27, 10 ng/ml BDNF and 10 ng/ml GDNF. The medium was changed weekly, and the following experiment was performed with the neurons after 3 weeks. The expression of TUJ1 (801202, Biolegend) was assessed in the neural cells via IF staining.

1.13 Differentiation of hESCs into Hepatocytes

This protocol followed a method previously published in Nature Protocols[36]. The hESCs were detached by 0.5 mM EDTA (Life Technologies, Camarillo, C, USA), seeded on VTN-N coated culture plates (Corning) and maintained for 48 hours in mTeSR 1 medium. Then, the medium was refreshed daily for all following steps. On days 1-2, the medium was replaced with fresh CDM-PVA (consisting of 0.5 g of PVA (Sigma) dissolved in 250 ml of IMDM/F-12, GlutaMAX (Invitrogen), 250 ml of IMDM (Invitrogen), 5 ml of chemically defined lipid concentrate (Invitrogen), 20 of thioglycerol 97% (Sigma), 350 of insulin (10 mg/ml; Roche), 250 of transferrin (30 mg/ml; Roche) plus Activin A (100 ng/ml; R&D), bFGF (80 ng/ml; R&D), BMP4 (10 ng/ml; R&D), and 10 mM of LY-294002 (Promega). On day 3, the cells were differentiated in RPMI Medium supplemented with Activin A (100 ng/ml) and bFGF (80 ng/ml). On days 4-6, the cells were expanded in RPMI medium supplemented with Activin A (50 ng/ml). On day 7, the cells were passaged and re-plated 105,000 cells/cm$^2$ cells in VTN-N coated culture plates in RPMI containing Activin A (50 ng/ml) and Y-27632 2HCl (10 μM Selleck-chem, Houston, TX, USA and Munich, Germany). Then, the cells were maintained in RPMI+Activin A (50 ng/ml) on days 8-11. The cells were differentiated into the hepatocyte endoderm and analyzed following the drug treatments. The expression of alpha-fetoprotein (A0008, Dako, Santa Clara, CA, USA) was analyzed in the hepatocyte endoderm via immunofluorescence staining.

1.14 Immunofluorescence Assay

The immunofluorescence assays were performed as previously described[29]. In brief, the cells were washed with PBS, fixed with 4% formaldehyde solution in PBS for 10 mins and permeabilized by 0.3% Triton X-100 for 10 mins. Then, the cells were stained with primary antibodies overnight at 4° C. After washing with PBS, the cells were incubated with Alexa Fluor® 488 anti-rabbit IgG or anti-mouse IgG for 1 hour at room temperature. The nuclei were stained with 4,6-diamidino-2-phenylindole (DAPI, 1 μg/ml).

1.15 Lentivirus Production and Cell Infection

The 293T cells were seeded with 10$^6$ cells in 6-well plates for the generation of the lentivirus. After 24 hours, the 293T cells were transfected with 1 μg of pLKO_AS3w.eGFP.bsd, 0.9 μg of pCMVR8.91, and 0.1 μg of pMD.G (National RNAi Core Facility, Taipei, Taiwan) via the TurboFect transfection reagent (Thermo Fisher Scientific). At 24 hours after the transfection, the medium was refreshed with the virus harvest medium, which contained HG-DMEM, 10% FBS and 1% BSA. The hBMMSCs were seeded in 6-well plates and later incubated with the lentivirus (multiplicity of infection=10) for one day. The cells were selected with 10 μg/ml blasticidin (Thermo Fisher Scientific) the following day. The GFP overexpressing hBMMSCs were then isolated using a cell sorter (FACS Aria™ II, BD Biosciences) and cultured in a medium containing 10 μg/ml blasticidin for the following experiments.

1.16 Kidney Capsule Transplantation

Mixtures of approximately $8 \times 10^5$ hESCs and $8 \times 10^5$ hBMMSCs were injected under the kidney capsules into 6-week-old male NSG mice. Five weeks after the transplantation, the animals were sacrificed, and the tissues were removed, fixed in 10% formalin, embedded in paraffin, stained with H&E or were subjected to IHC staining. The staining protocols were described in the materials and method section. Chicken anti-GFP (ab 13970, Abcam, Cambridge, MA, USA) antibody was used for the GFP overexpressing hBMMSCs IHC staining.

1.17 Alamar Blue Assay.

Alamar blue assay measured the relative cell number. In the cells, we added ¹⁄₁₀ of Alamar Blue Viability Assay reagent to the total volume of the mixture (Biotium; Fremont, CA, USA). The cells were incubated overnight at 37° C. The resulted were quantified by the measurement of optical density (OD) absorbance values at 570 nm and 600 nm, and the relative cell number was calculated.

1.18 Statistical Analysis

All statistical data are presented as the mean±standard deviation (S.D.) of at least three biological replicates. Statistically significant differences were assessed by t test or One-Way ANOVA, where p-value <0.05 was considered a significant difference.

2. Results 2.1 Differential Expression of the Alpha Subunit of Na$^+$/K$^+$-ATPase in hESCs and hBMMSCs Because not all cancer signals overlap with hESC signals, we determined the expression levels of cardiac glycosides target genes, Na$^+$/K$^+$-ATPase, to evaluate whether they can eliminate the undifferentiated hESCs. It has previously been reported that cardiac glycosides have anti-cancer effects by targeting Na$^+$/K$^+$-ATPase[25,26]. Via a western blot analysis, we found that the hESCs expressed Na$^+$/K$^+$-ATPase more abundantly than adult stem cells, such as human bone marrow mesenchymal stem cells (hBMMSCs) (FIG. 1A). This finding suggests that hESCs may be more sensitive to cardiac glycosides than hBMMSCs due to their differential expression of Na$^+$/K$^+$-ATPase.

2.2 Digoxin and Lanatoside C-Induced Cell Death in hESCs but not in hBMMSCs

Figure 1B:
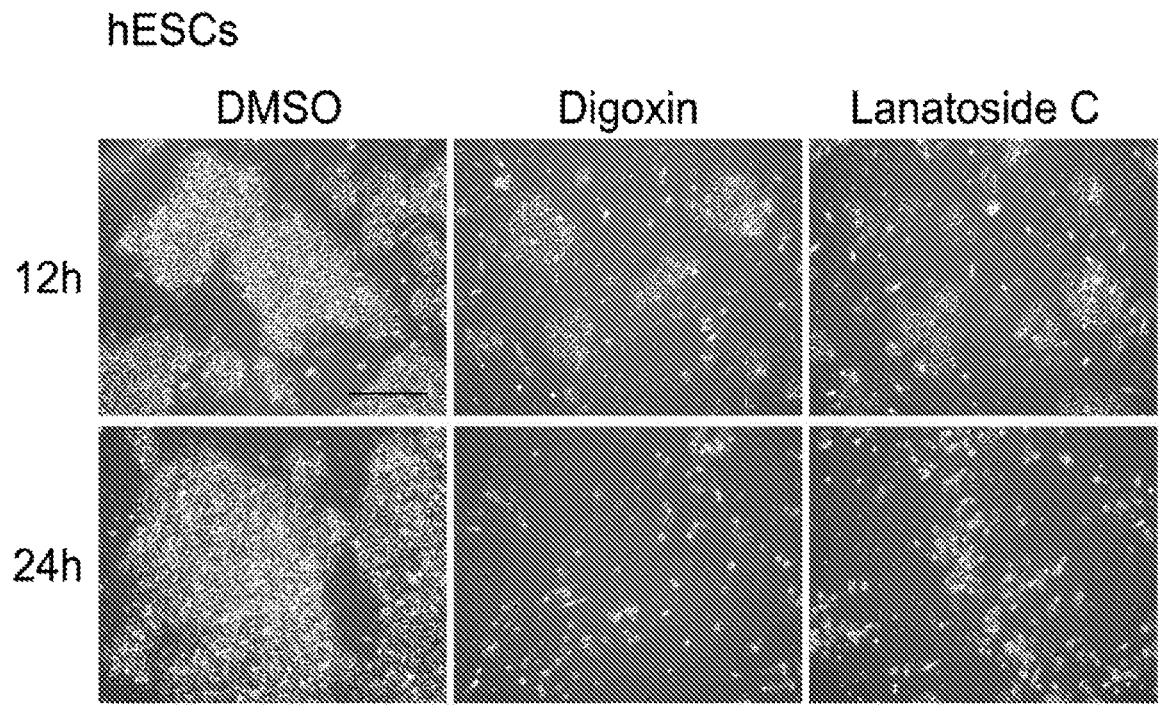
Figure 1C:
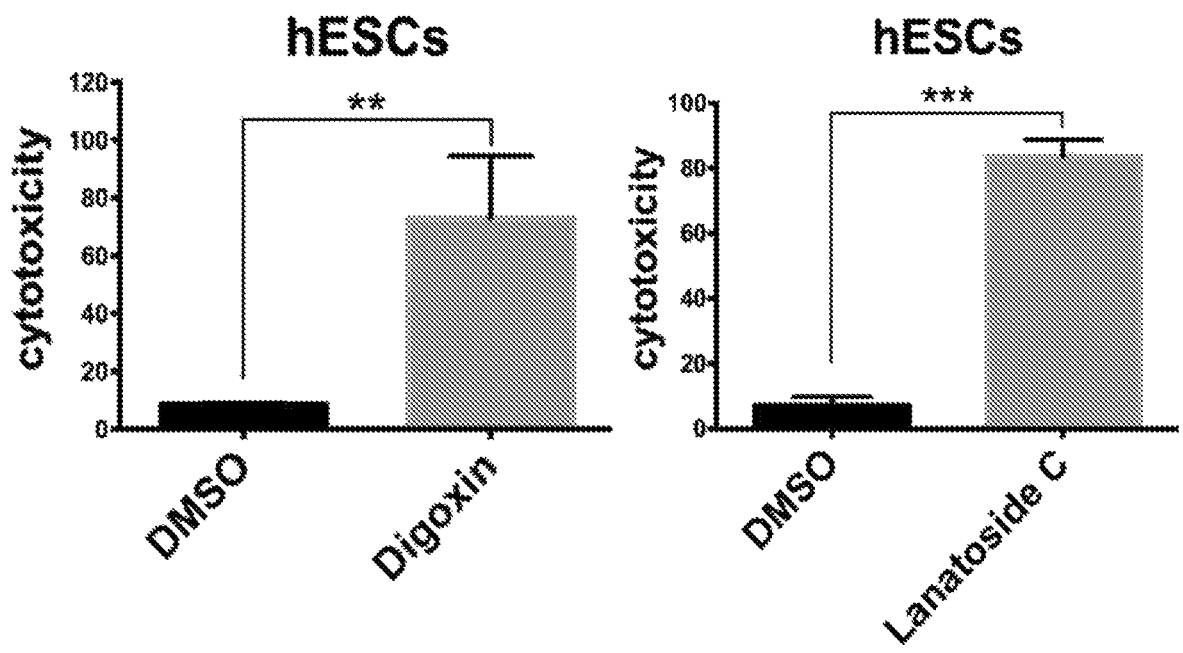
Figure 6A:
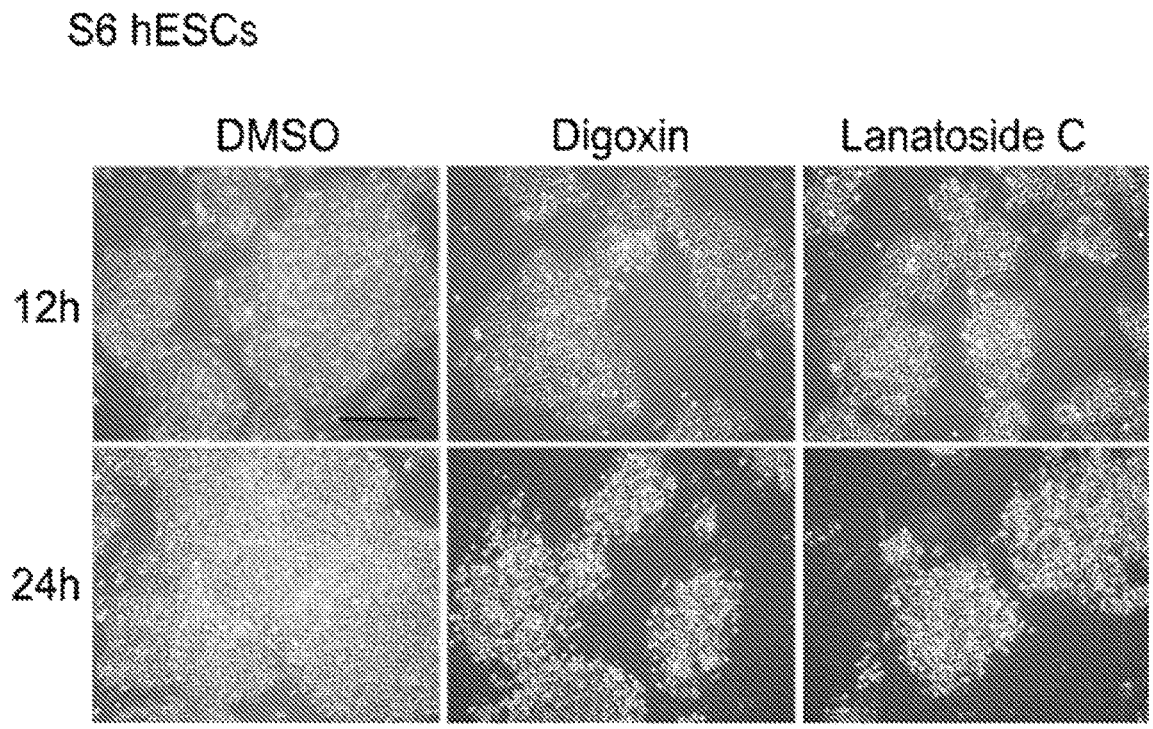
FIG. 6A to FIG. 6B include charts showing that cardiac glycosides caused cytotoxicity in HUES6 hESCs.
Figure 6B:
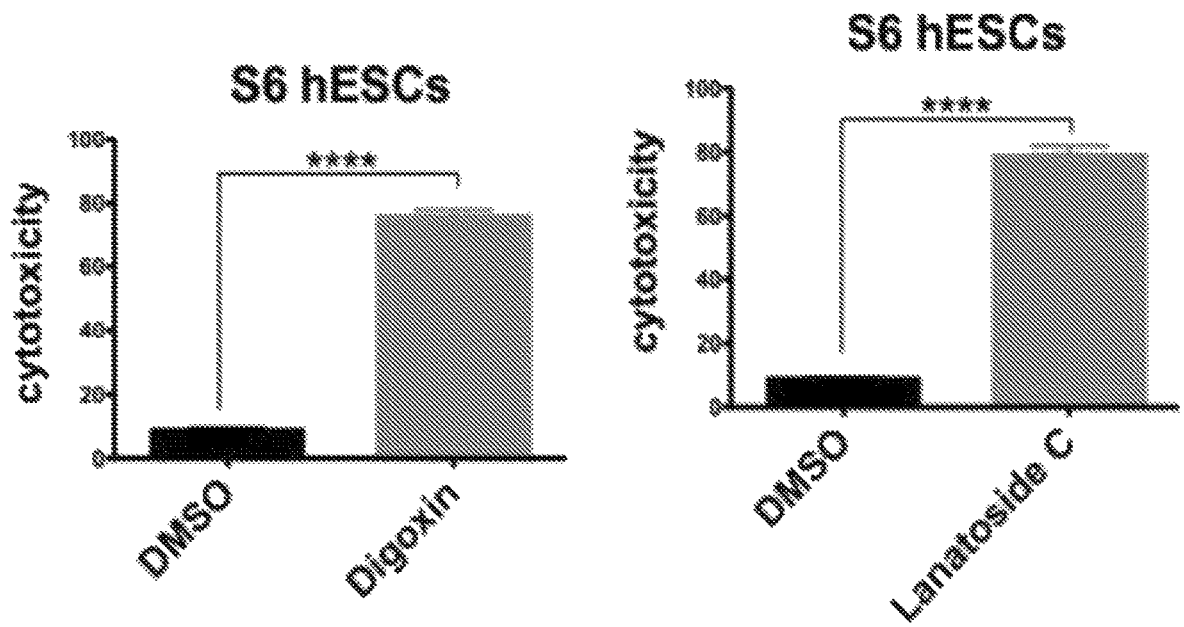

We investigated whether cardiac glycosides affected the viability of hESCs or other cell types. First, we treated undifferentiated hESCs with digoxin and lanatoside C for 12 hours and 24 hours, respectively. Both digoxin (2.5 μM) and lanatoside C (2.5 μM) induced dramatic cell death in the hESCs (FIG. 1B). To investigate the cytotoxic effect of the cardiac glycosides, we measured the release of LDH in the culture supernatants after the hESCs were treated with digoxin or Lanatoside C for 24 hours (FIG. 1C). Both drugs significantly induced a cytotoxic effect in the hESCs (FIG. 1C). Consistently, in another hESC line, i.e., HUES6, both digoxin (2.5 μM) and lanatoside C (2.5 μM) induced cell death (FIG. 6A) and cytotoxicity (FIG. 6B).

Figure 1D:
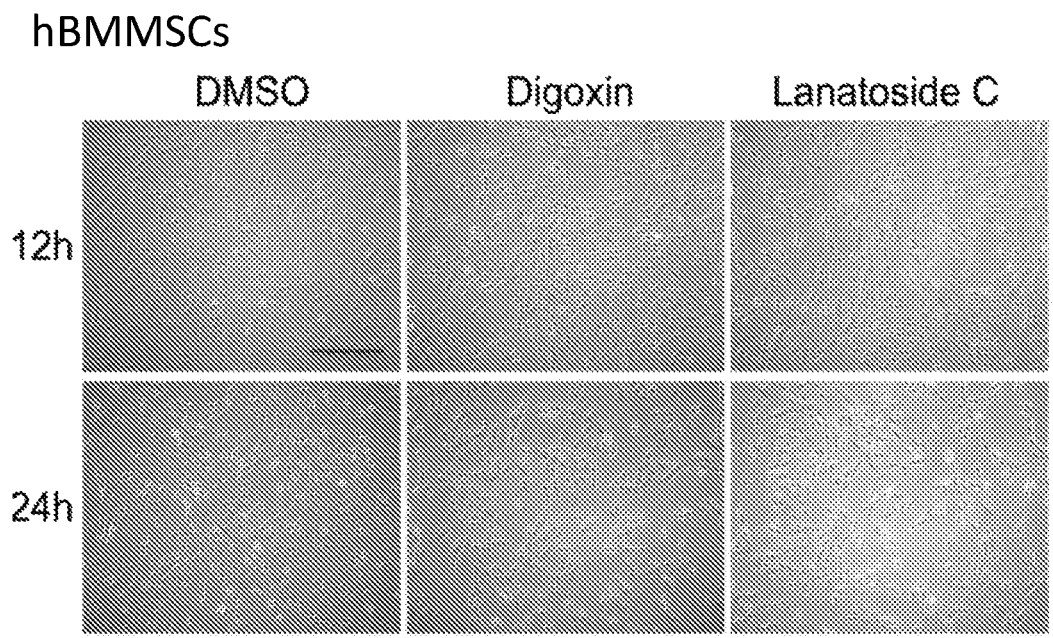
Figure 1E:
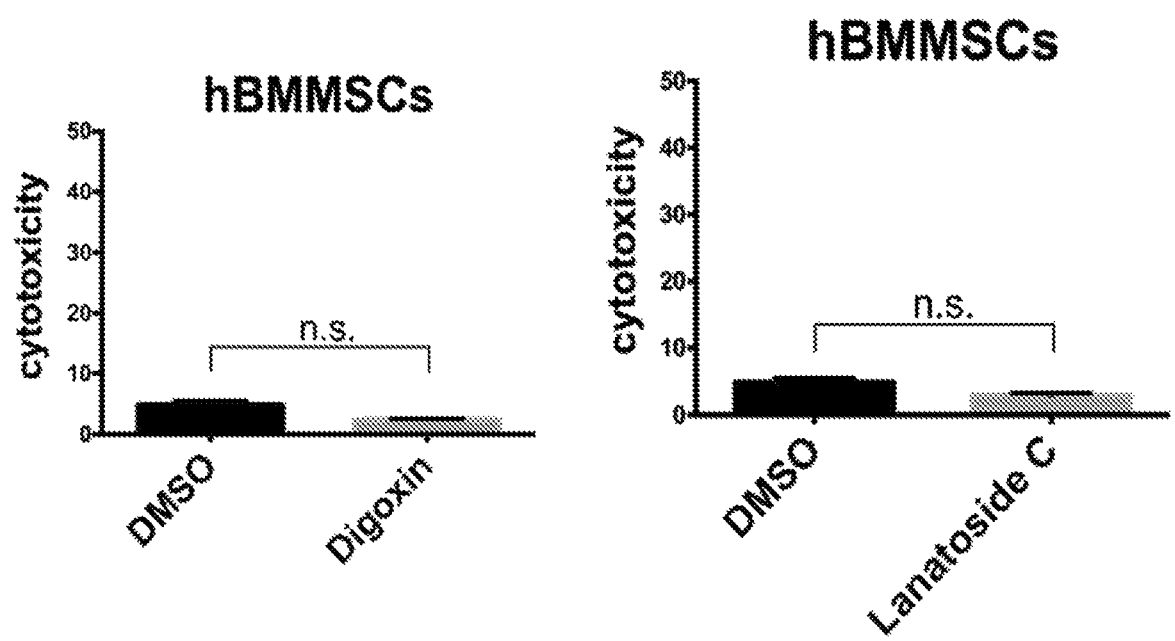

In contrast, digoxin and lanatoside C did not affect the survival of hBMMSCs (FIG. 1D). Both drugs had no cytotoxic effects on the hBMMSCs as measured by the LDH cytotoxic assay (FIG. 1E).

Figure 7:
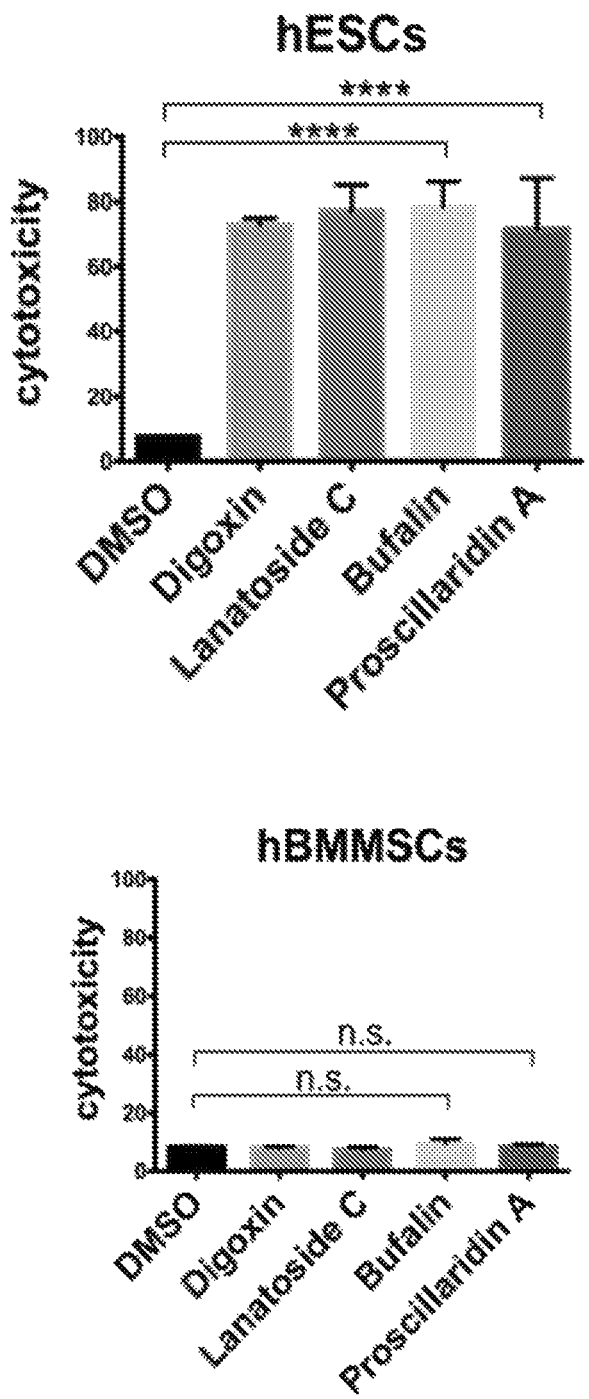
FIG. 7 shows that the bufadienolide subgroup of cardiac glycosides, i.e., bufalin and proscillaridin A, induced a cytotoxic effect in hESCs but did not affect hBMMSCs. hESCs (upper panel) and hBMMSCs (lower panel) were individually treated with different cardiac glycosides at a final concentration of 2.5 µM for 24 hours. The cytotoxic effect was measured by an LDH release assay, and all data were compared with the DMSO solvent control. Cardenolide: digoxin and lanatoside C; bufadienolides: bufalin and proscillaridin A. ****P<0.0001; n.s. not significant. Data are shown as the mean SD.

Cardiac glycosides can be divided into two subgroups based on the natural structure of their lactone moiety[23,26]. Digoxin and lanatoside C belong to a cardenolides subgroup that has butyrolactone[23]. We choose two drugs in the bufadienolides subgroup that have a pyrone ring[23]. We used bufalin or proscillaridin A to treat the hESCs and hBMMSCs. The results were similar to the results of the digoxin- and lanatoside C-treated cells in which bufalin or proscillaridin A induced cytotoxicity in the hESCs but not in the hBMMSCs (FIG. 7).

Figure 2A:
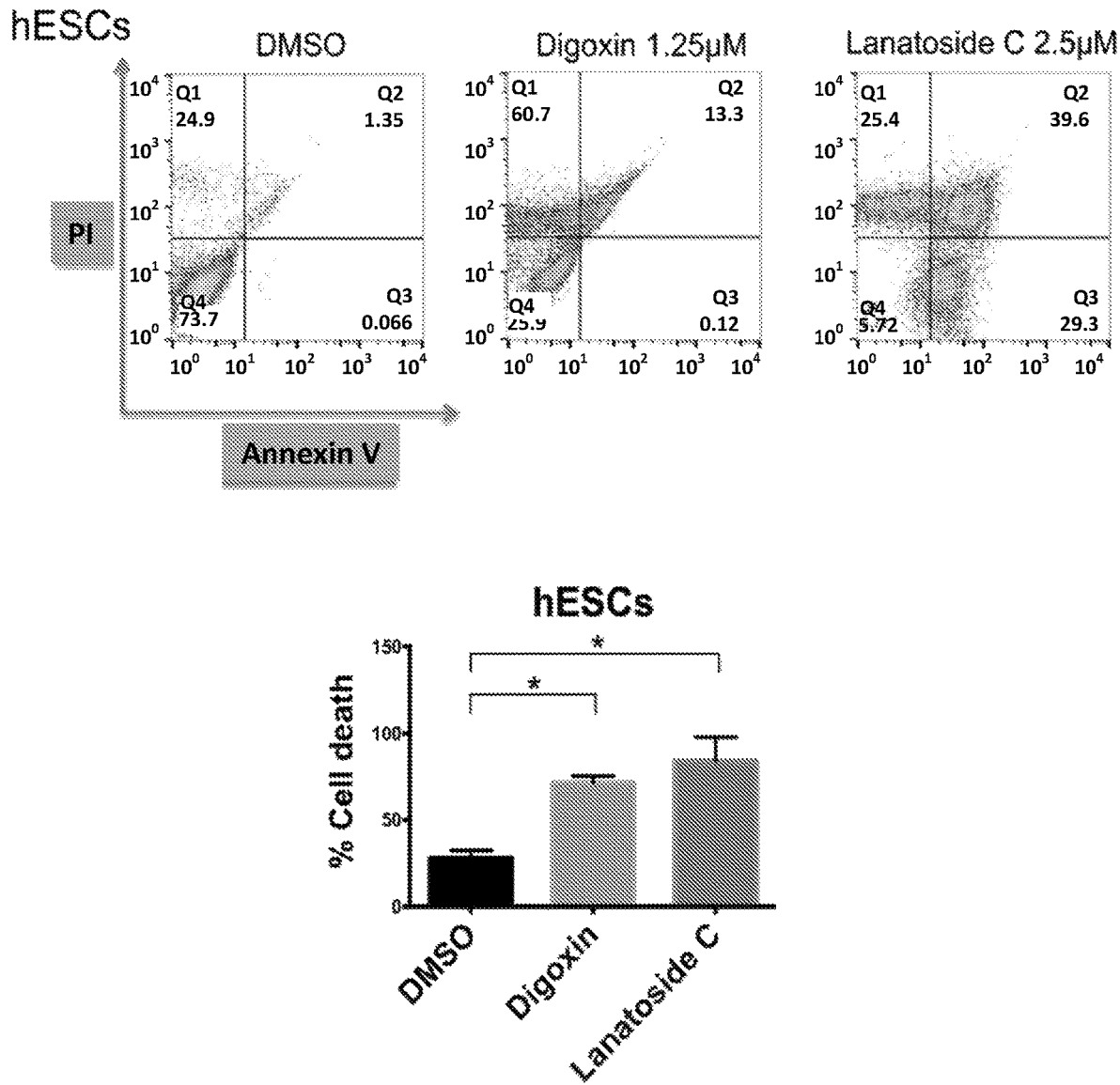
FIG. 2A to FIG. 2D include charts showing that cell death markers were upregulated in the cardiac glycoside-treated hESCs but not in the hBMMSCs. Cell death was analyzed using hESCs or MSCs.
Figure 2B:
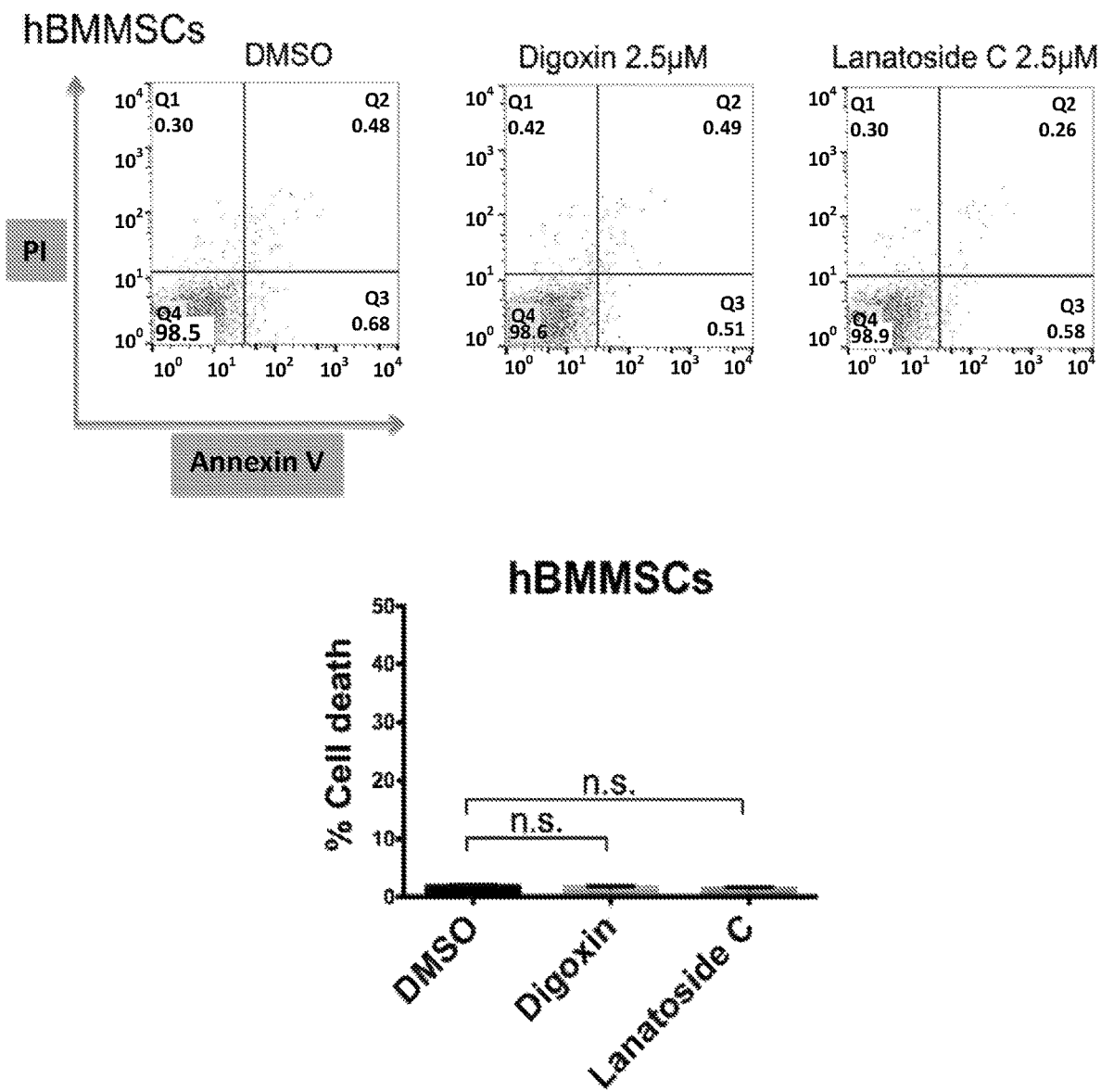
Figure 2C:
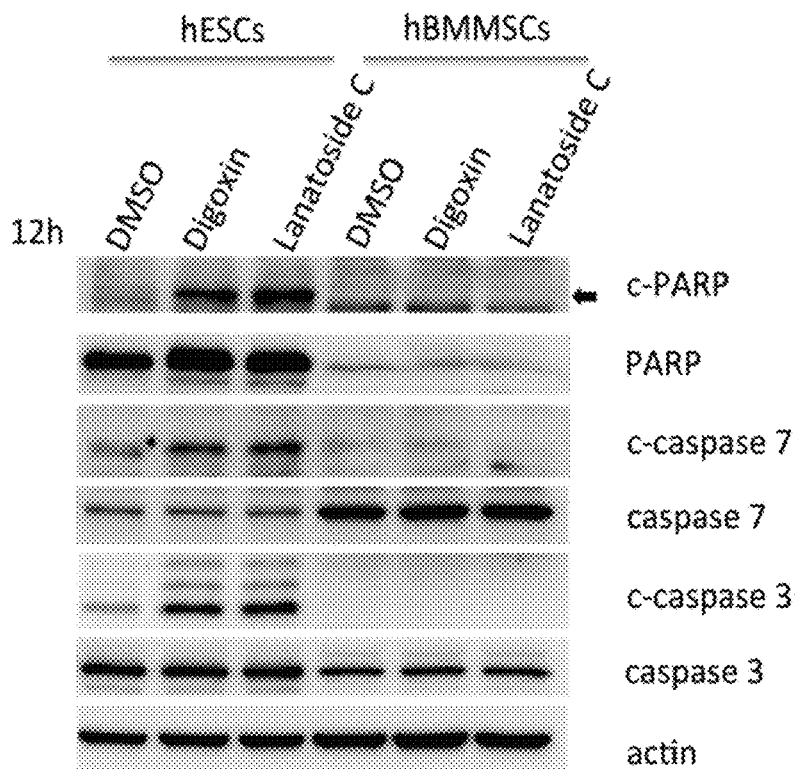
Figure 2D:
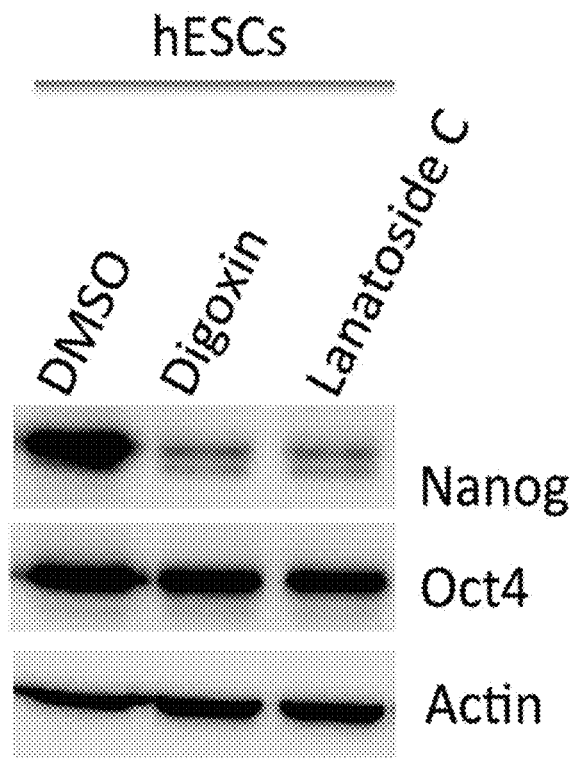

To determine whether the cytotoxic effect of the cardiac glycosides is selective to hESCs, we also performed a PI/Annexin flow cytometry analysis. After treating the cells for 24 hours, the cell death reached 70% following the digoxin treatment and 82% following the lanatoside C treatment (FIG. 2A). In contrast, more than 98% of the cells were alive in the digoxin- or lanatoside C-treated hBMMSCs (FIG. 2B). In addition, we observed increases in the cleaved form of PARP, caspase-3, and caspase-7 in the digoxin- and lanatoside C-treated hESCs (FIG. 2C). In contrast, no cleaved form of the apoptosis markers was detected in the hBMMSCs treated with digoxin or lanatoside C (FIG. 2C). In addition to the induction of cell death, the tumorigenic potential of the remaining of hESCs was abolished upon cell differentiation. After the hESCs were treated with digoxin or lanatoside C for 12 hours, the protein levels of Nanog were downregulated (FIG. 2D). Nanog is a part of the core transcriptional regulatory networks in ESCs. Loss of Nanog in the hESCs can induce extraembryonic lineage differentiation[37]. Nanog has been reported to play important roles in hESC pluripotency and self-renewal[38]. These results suggested that cardiac glycosides induce cell death in hESCs but not in hBMMSCs.

Figure 12:
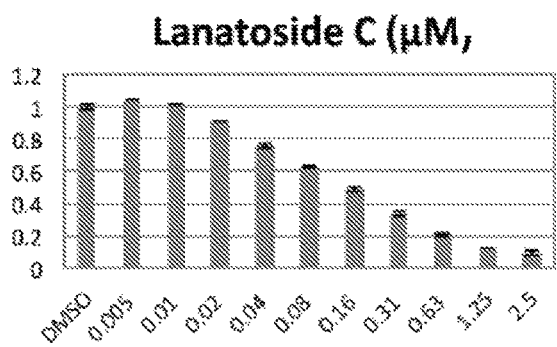
FIG. 12 shows that cardiac glycosides (digoxin, lantoside C, proscillaridin A, digitoxin, digitoxigenin, ouabain) induced cytotoxic effect of in hESCs in a dose dependent manner.
Figure 12:
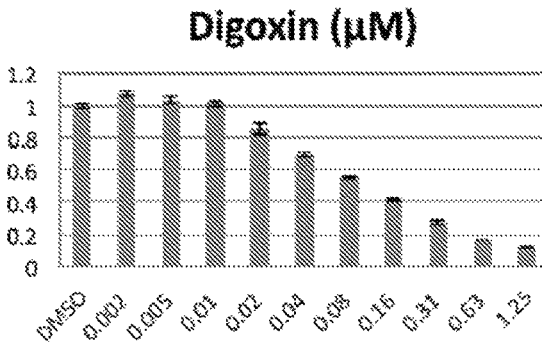
Figure 12:
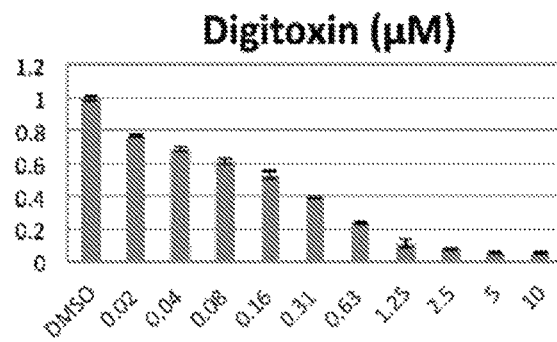
Figure 12:
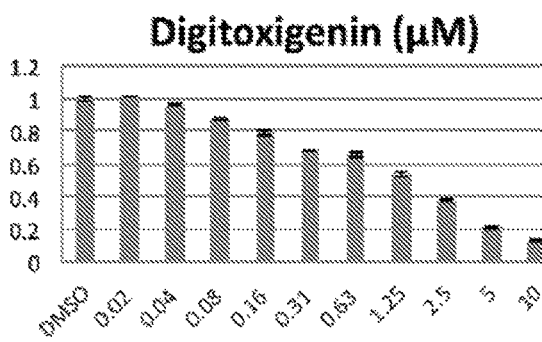
Figure 12:
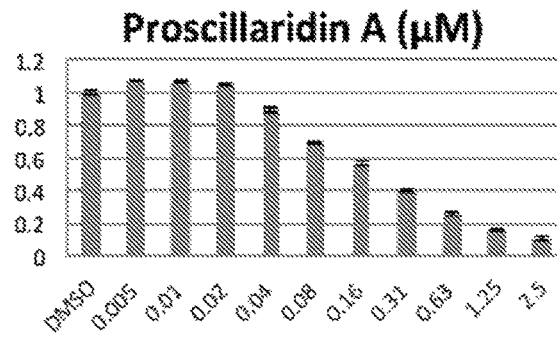
Figure 12:
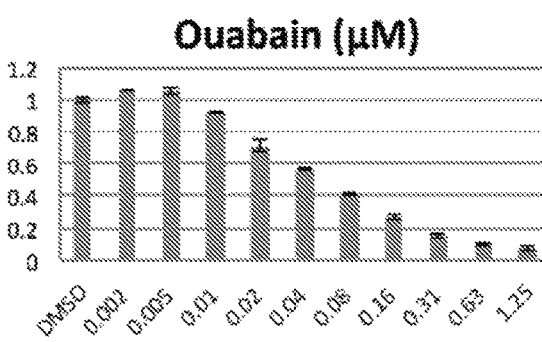

In addition, Alamar blue assay was conducted. Digoxin, lantoside C, proscillaridin A, digitoxin, digitoxigenin, and ouabain-induced cell death in hESCs in dose dependent manner (FIG. 12)

Figure 3A:
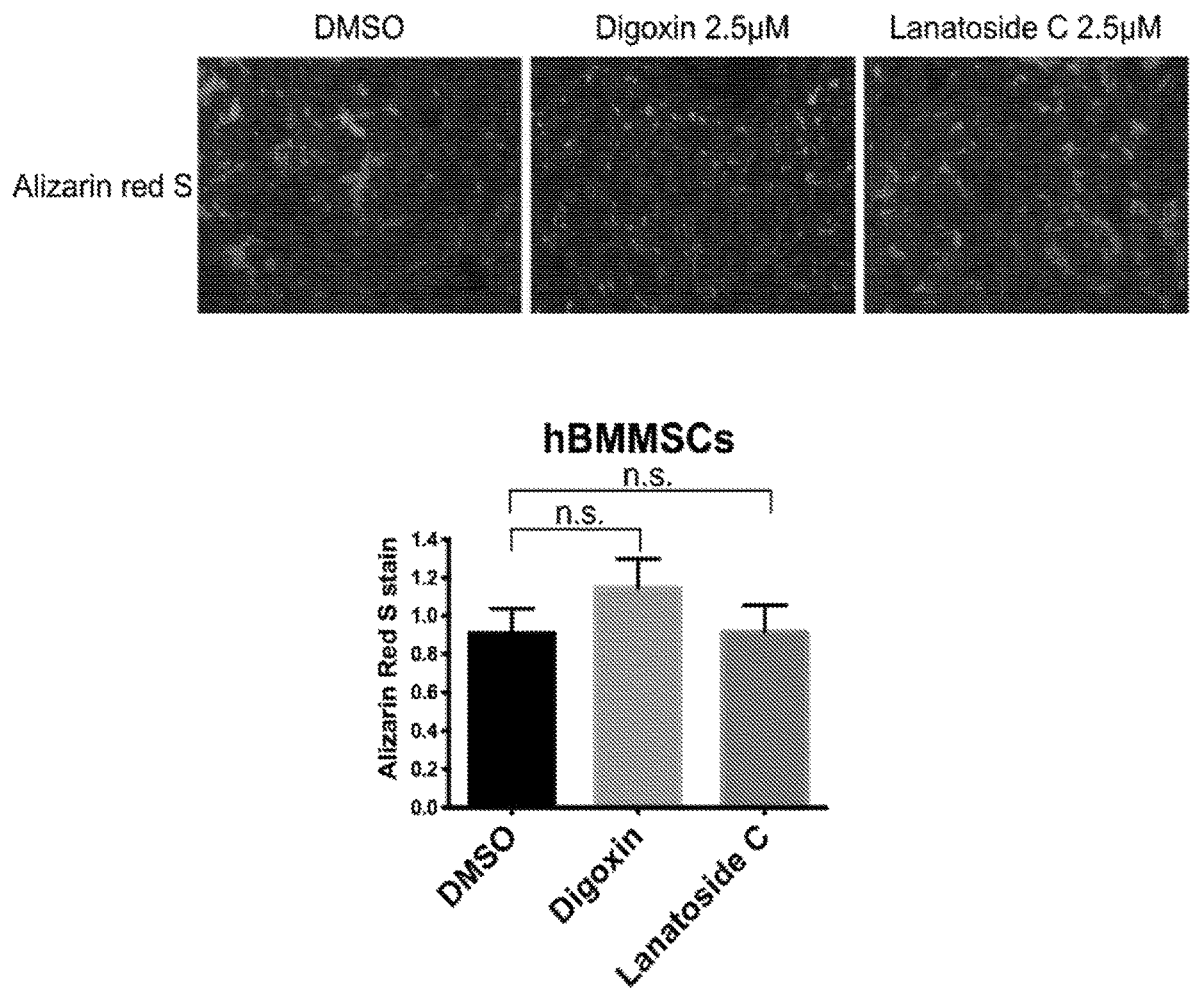
FIG. 3A to FIG. 3C include charts showing that cardiac glycoside treatment of hBMMSCs did not affect the differentiation abilities. hBMMSCs were treated with DMSO, 2.5 μM digoxin, or 2.5 μM lanatoside C for 24 hours, and the drugs were removed for further differentiation.
Figure 3B:
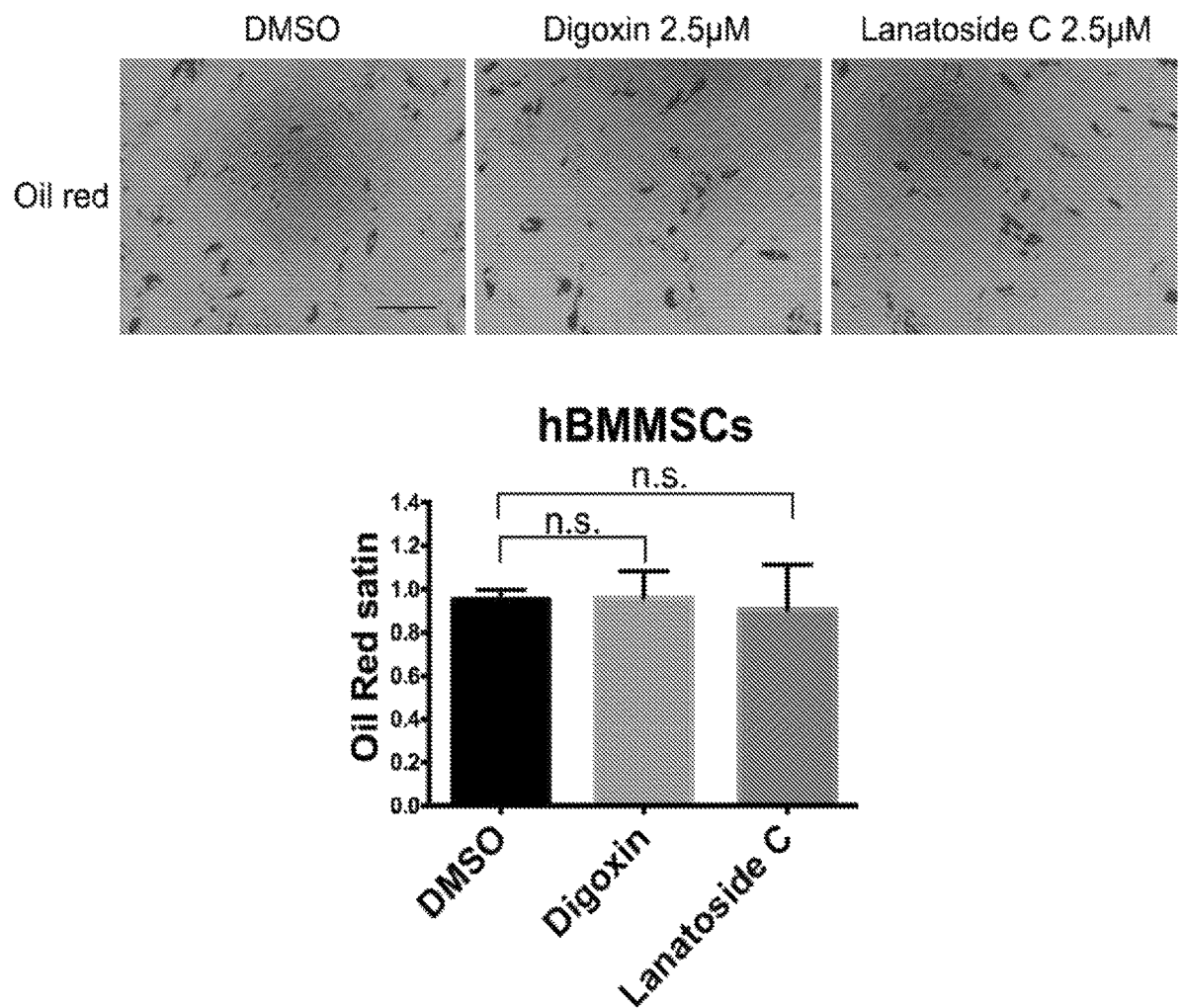
Figure 3C:
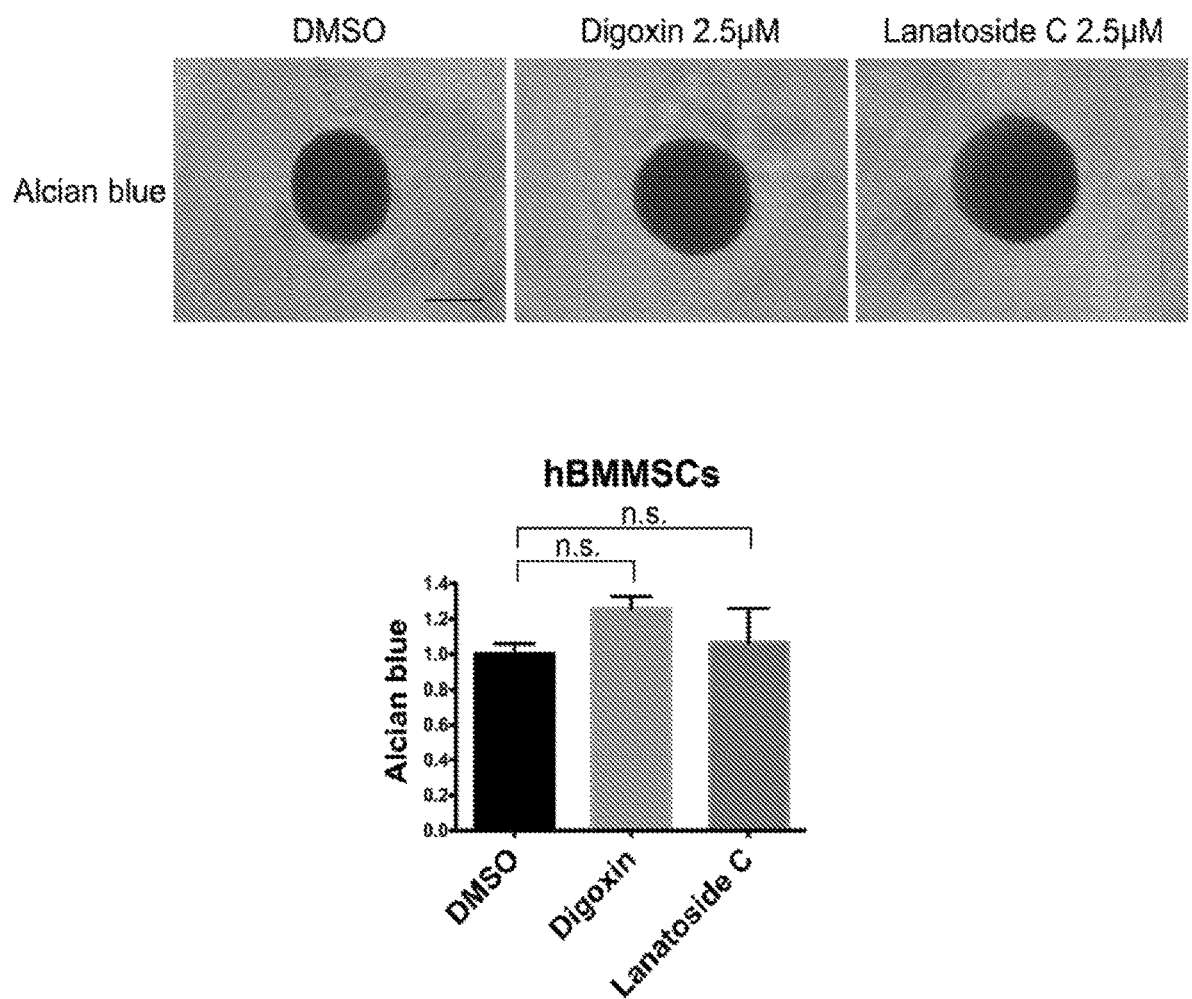

2.3 Differentiation Abilities of hBMMSCs into Three Lineages are not Affected by the Digoxin or Lanatoside C Treatment We demonstrated that the cardiac glycosides did not affect the survival of hBMMSCs. MSCs are multipotent cells that are promising for regenerative medicine. MSCs can be specifically induced into osteoblasts, adipocytes, and cartilage cells[39]. To determine whether the differentiation ability of hBMMSCs is affected by digoxin or lanatoside C, we performed a differentiation assay. Digoxin or lanatoside C was removed after treating the hBMMSCs for 24 hours, and the cells were differentiated into three lineages. Notably, neither digoxin nor lanatoside C affected the differentiation ability of the hBMMSCs into osteoblasts (FIG. 3A), adipocytes (FIG. 3B), and chondrocytes (FIG. 3C). Based on these results, cardiac glycosides do not influence the multipotency of hBMMSCs.

Figure 4A:
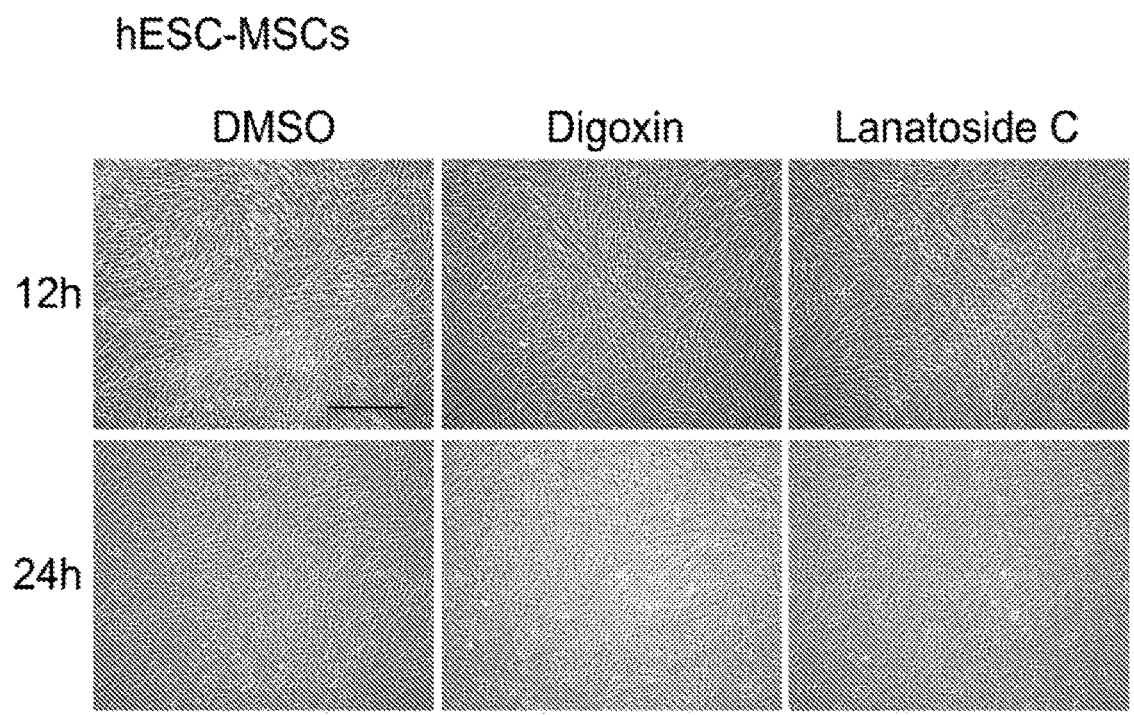
FIG. 4A to FIG. 4E include charts showing that cardiac glycosides did not affect the cell viability of H9 hESC-derived MSCs.
Figure 4B:
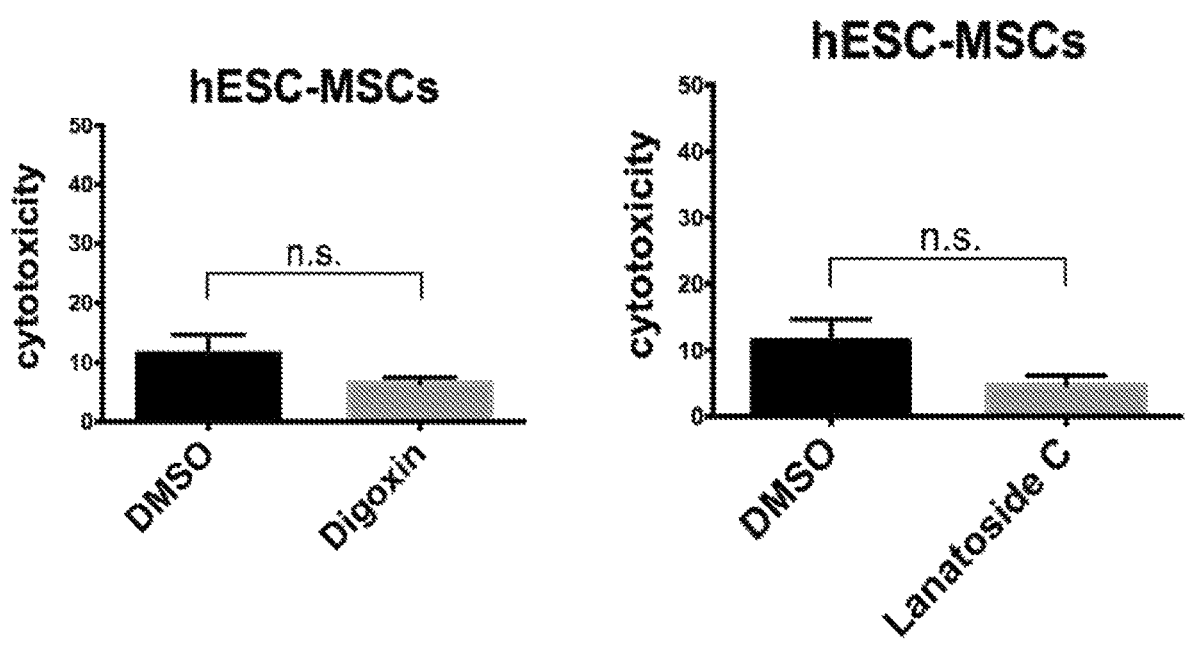
Figure 8A:
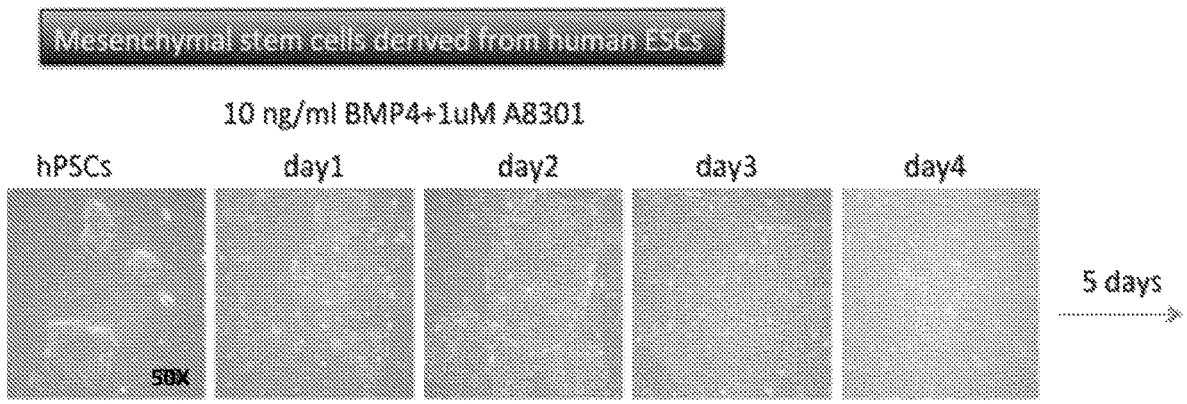
Figure 8A:
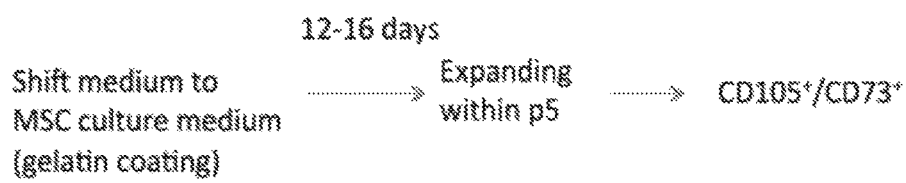
Figure 8B:
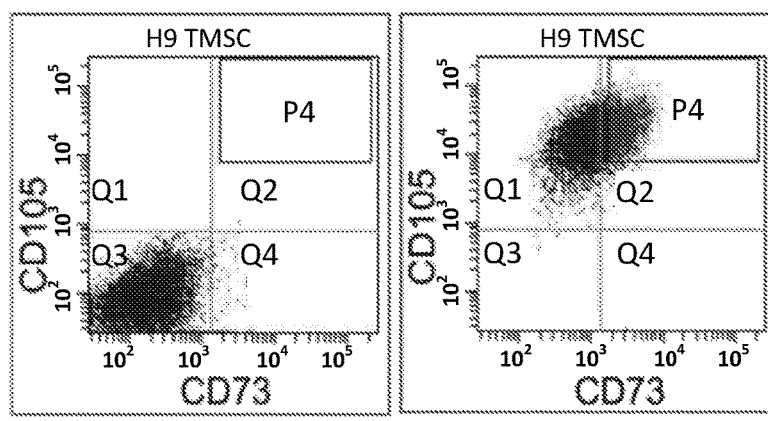
Figure 8D:
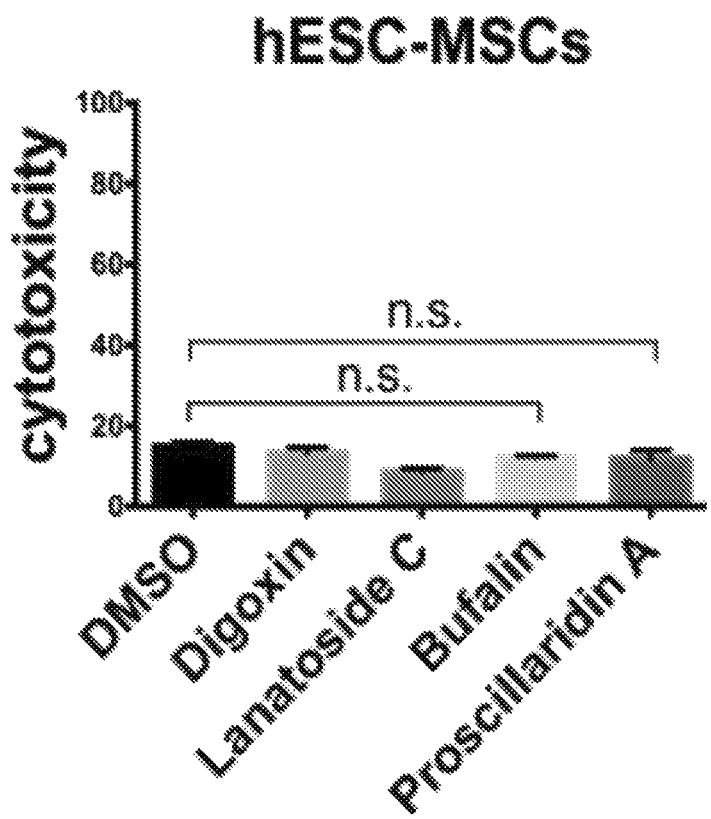

2.4 Digoxin or Lanatoside C Did not Induce Cytotoxic Effects in hESC-Derived MSCs To further validate the effects of the cardiac glycosides in hESCs and hESC-derived cell types, we first choose hESC-derived MSCs (hESC-MSCs) as our model. Dr. Xu and colleagues provided a simple and fast method to induce hESCs into hMSCs using a two-step approach[30] (FIG. 8A-C). We differentiated the H9 hESCs into MSCs and examined whether the cardiac glycosides affected the viability of the hESC-MSCs. The hESC-MSCs were treated with digoxin and lanatoside C for 12 hours and 24 hours, respectively. Neither digoxin (2.5 µM) nor lanatoside C (2.5 µM) induced cell death in the H9 hESC-MSCs (FIG. 4A). To investigate the cytotoxic effect of the cardiac glycosides, we measured the release of LDH in the culture supernatants after treating the H9 hESC-MSCs with digoxin or Lanatoside C for 24 hours. Neither Digoxin nor lanatoside C affected the survival of the H9 hESC-MSCs (FIG. 4B). In addition to digoxin and lanatoside C, we also found that bufalin or proscillaridin A do not induce cytotoxicity (FIG. 8D). This result is consistent with the effect observed in the hBMMSCs (FIG. 7).

Figure 4C:
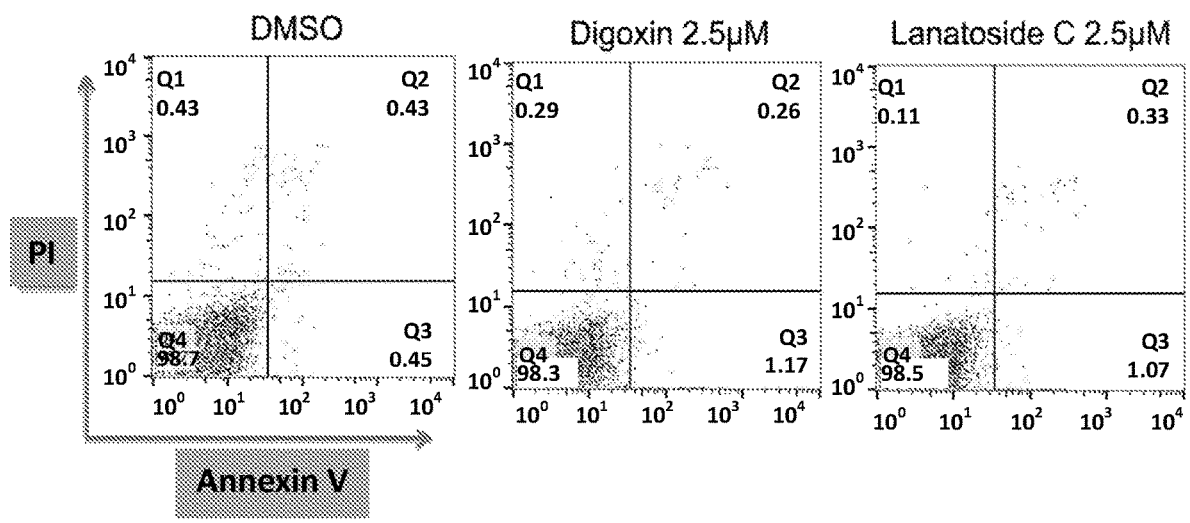
Figure 4C:
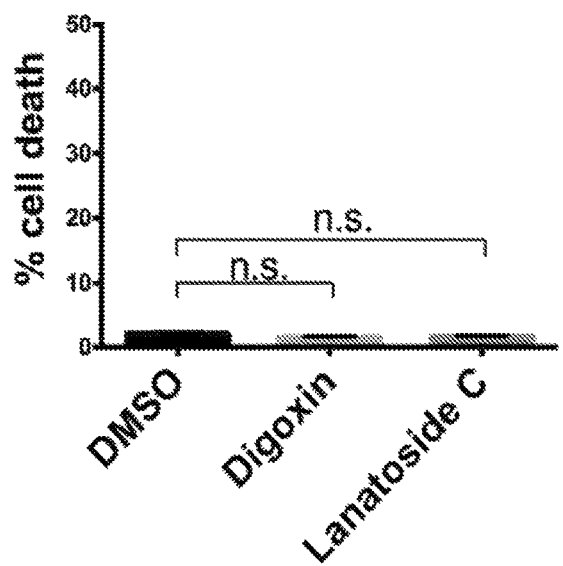
Figure 4D:
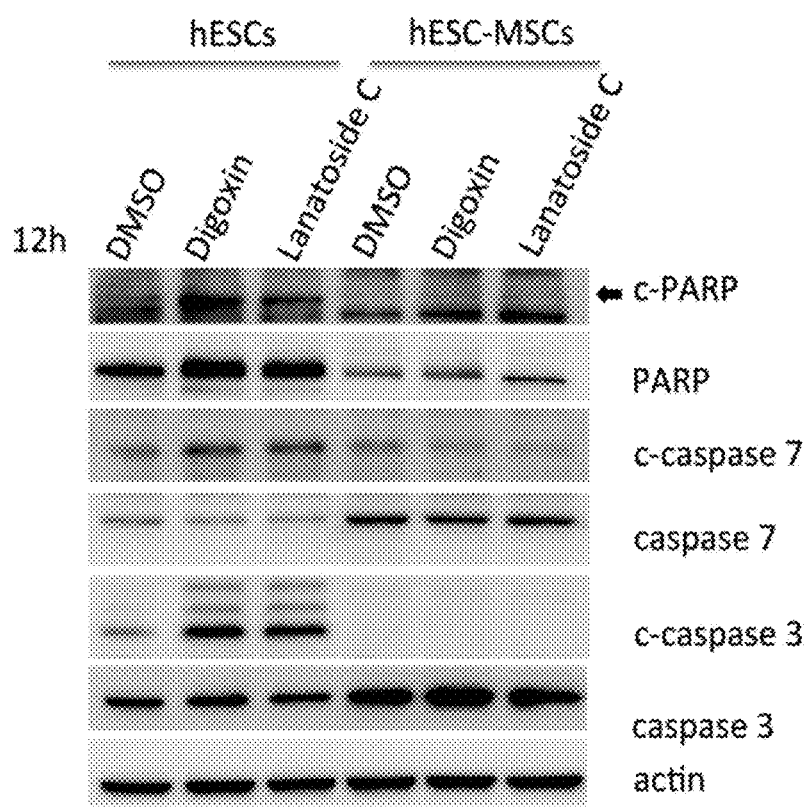

To investigate whether the cardiac glycosides induced cell death in the H9 hESC-MSCs, PI/Annexin flow cytometry and western blot analyses were performed. After treating the hESC-MSCs with digoxin or lanatoside C for 24 hours, the cell death was less than 2% (FIG. 4C). Consistently, no cleaved form of the apoptosis markers was detected in the hESC-MSCs treated with digoxin or lanatoside C (FIG. 4D). These results suggested that the cardiac glycosides did not induce cell death in the H9 hESC-MSCs. In addition, $Na^+/K^+$-ATPase was abundantly expressed in the undifferentiated hESCs but not in the hESC-MSCs (FIG. 4E), which might demonstrate that the toxicity of the cardiac glycosides is limited to the undifferentiated hESCs.

Figure 9A:
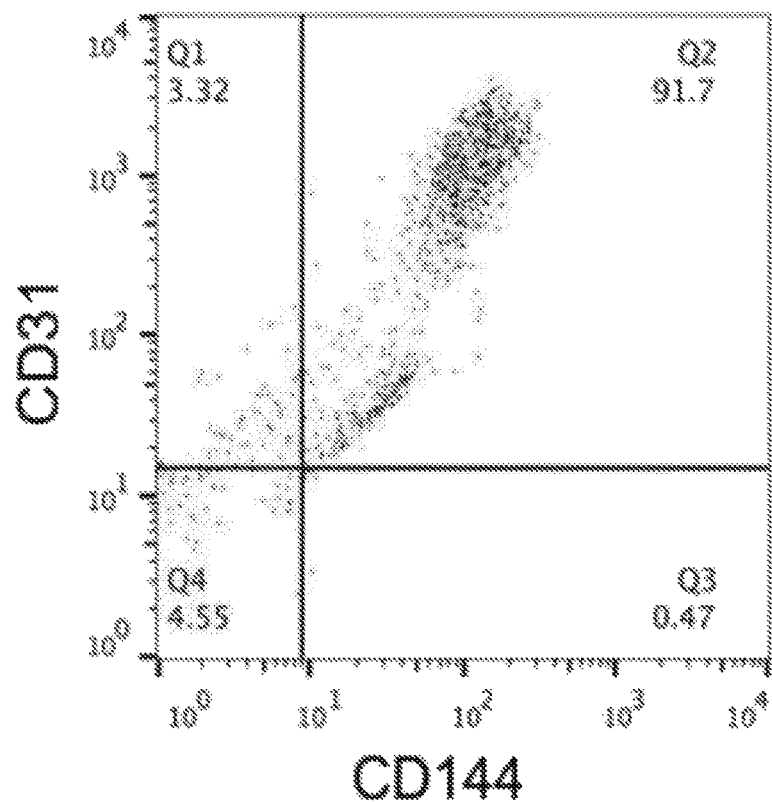
FIG. 9A to 9G include charts showing that cardiac glycosides did not or slightly affect the survival of hPSC derived cells.
Figure 9B:
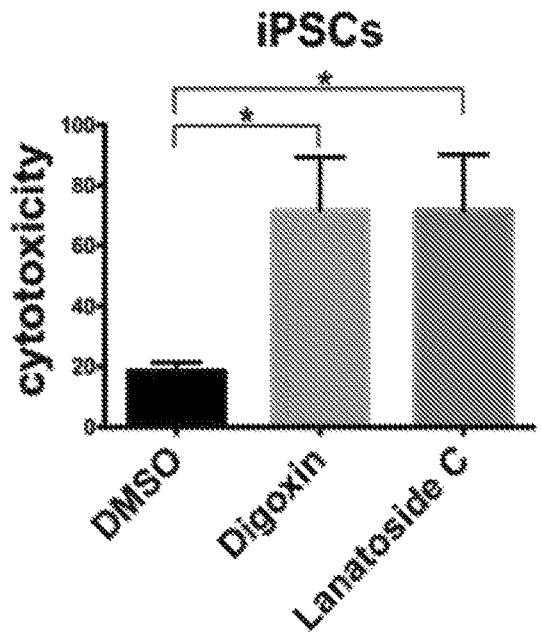
Figure 9C:
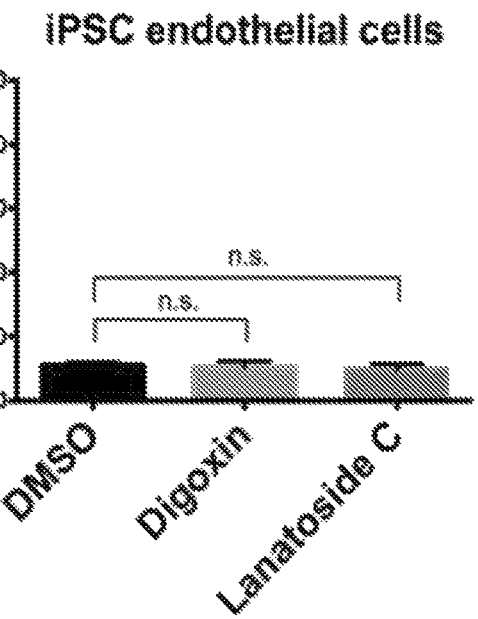
Figure 9D:
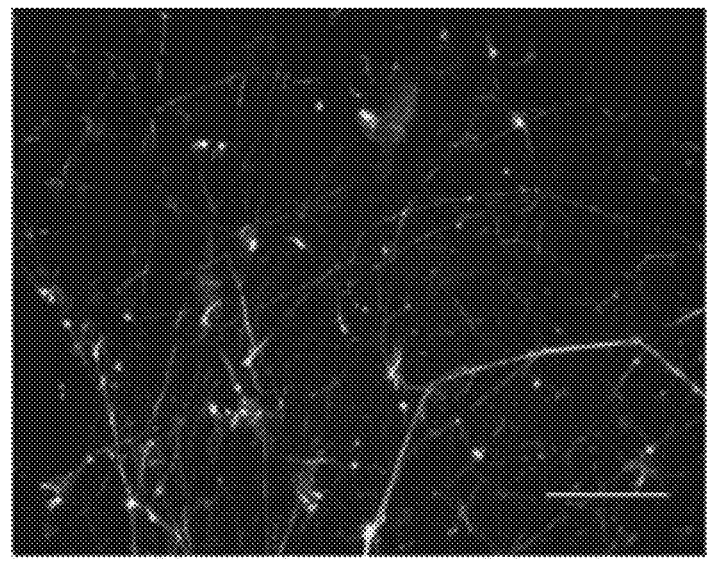
Figure 9E:
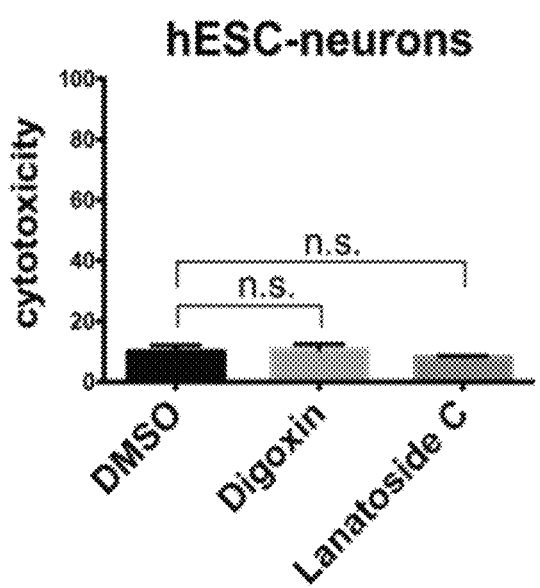
Figure 9F:
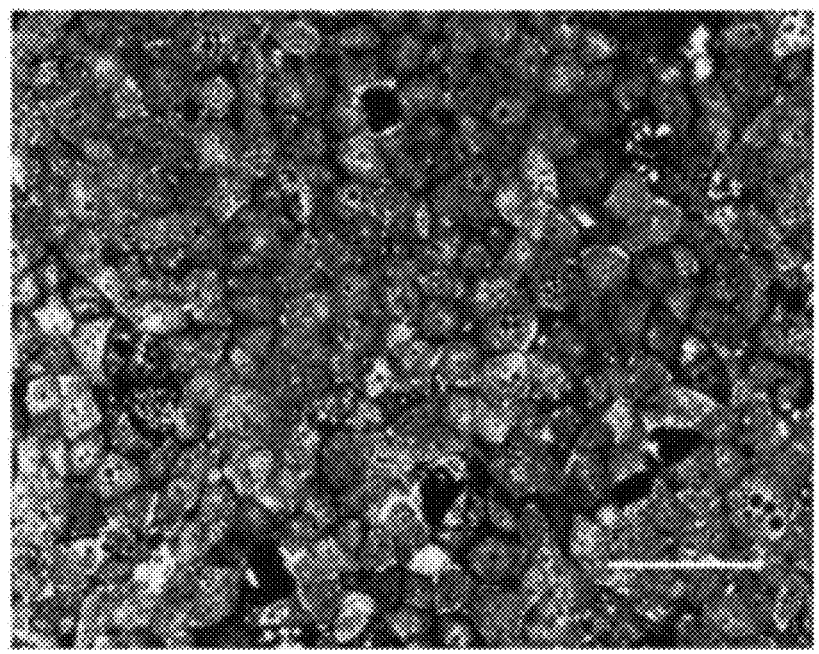
Figure 9G:
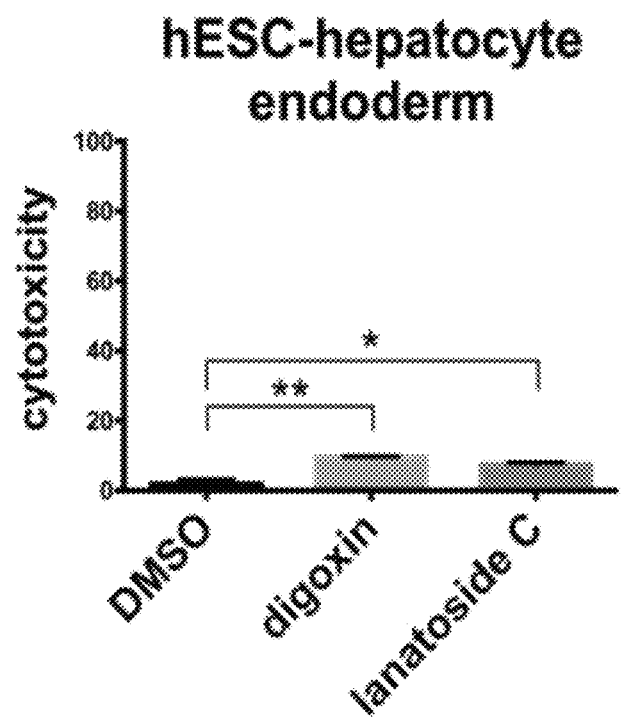

2.5 Digoxin and Lanatoside C Did not or Slightly Induce Cell Death in hPSCs Derived Endothelium Cells, Neurons, or Hepatocyte Endoderm We next tested whether digoxin and lanatoside C affected other hPSC-differentiated cell types. The mesoderm lineage of $CD34^+/CD144^+$ hiPSC-derived endothelial cells was obtained from Dr. Chiang and his colleagues (National Cheng Kung University, Tainan, Taiwan) (FIG. 9A). Undifferentiated hiPSCs and hiPSCs-derived endothelial cells were exposed to digoxin or lanatoside C for 24 hours. After the treatment, digoxin and lanatoside C induced cytotoxicity in the hiPSCs (FIG. 9B), but the hiPSC-derived endothelial cells remained alive (FIG. 9C). We differentiated the H9 hESCs into TUJ1-positive neurons that belong to the ectoderm (FIG. 9D) and then treated these hESC-neurons with digoxin or lanatoside C for 24 hours. Digoxin and lanatoside C did not induce cytotoxicity in the neuronal cells (FIG. 9E). In addition, we differentiated the hESCs into AFP-expressing hepatocyte endoderm, which belongs to the endoderm (FIG. 9F). The results showed that the drugs slightly, if at all, induced any cell death in the hepatocyte endoderm cells (less than 10%) (FIG. 9G). Based on the abovementioned results, digoxin and lanatoside C might specifically induce cell death in undifferentiated hPSCs but not in their differentiated progeny.

We also tested the cytotoxic effects of other cardiac glycosides, including ouabain, digitoxin, digitoxigenin, proscillaridin A and bufalin on undifferentiated pluripotent stem cells, hESCs and hPSCs, and various differentiated cells including MSCs, neuron cells, hepatocyte endoderm cells. The results are summarized below.

TABLE 1

| Cardiac glycosides | mesenchymal stem cells | neuron cells | endothelial cells | hepatocyte endoderm cells* | hESCs** | hiPSCs** |
|---|---|---|---|---|---|---|
| Digoxin | − | − | − | −/+ | +++ | +++ |
| Lanatoside C | − | − | − | −/+ | +++ | +++ |
| Ouabain | − | − | − | −/+ | +++ | +++ |
| Digitoxin | − | − | − | −/+ | +++ | +++ |
| Digitoxigenin | − | − | − | −/+ | +++ | +++ |
| Proscillaridin A | − | − | − | −/+ | +++ | +++ |
| Bufalin | − | − | − | −/+ | +++ | +++ |

*10% positive cells;
**more than 70% positive cells

2.6 Digoxin and Lanatoside C Prevent Teratoma Formation in NSG Mice

Figure 5A:
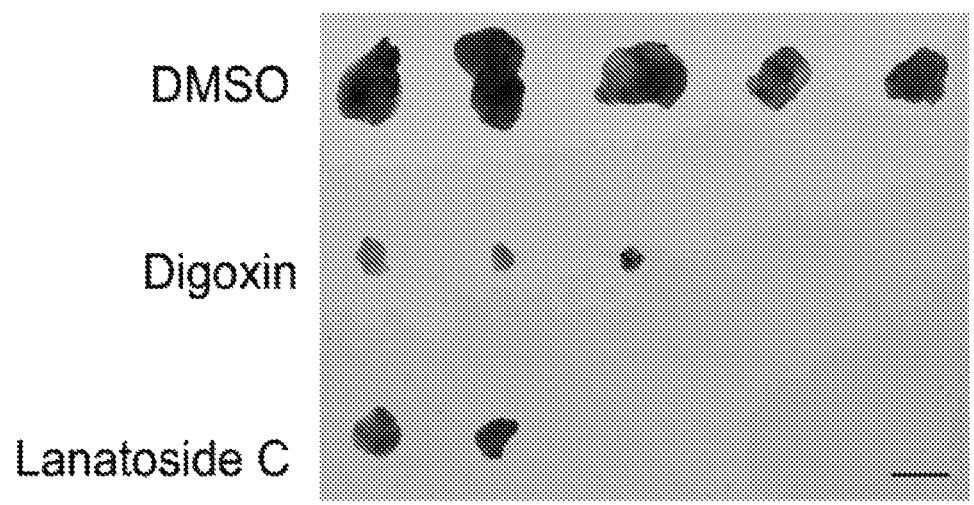
FIG. 5A to FIG. 5C include charts showing that cardiac glycosides treatment prevented teratoma formation in hESCs in NSG mice. Tumors from NSG mice transplanted with DMSO-, digoxin-, or lanatoside C-treated cells for two months (n=8 in each group). Scale bar: 10 mm.
Figure 5B:
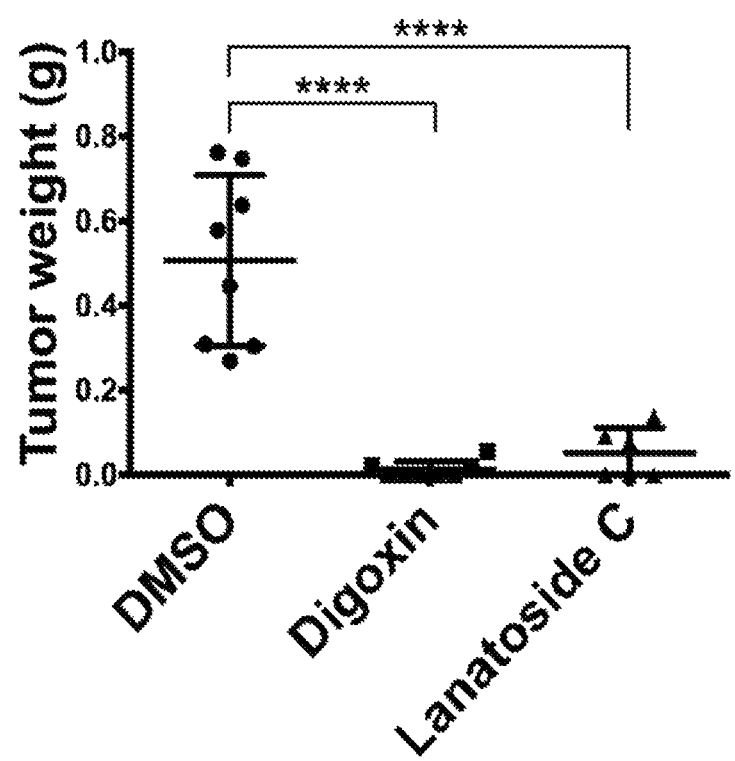
Figure 5C:
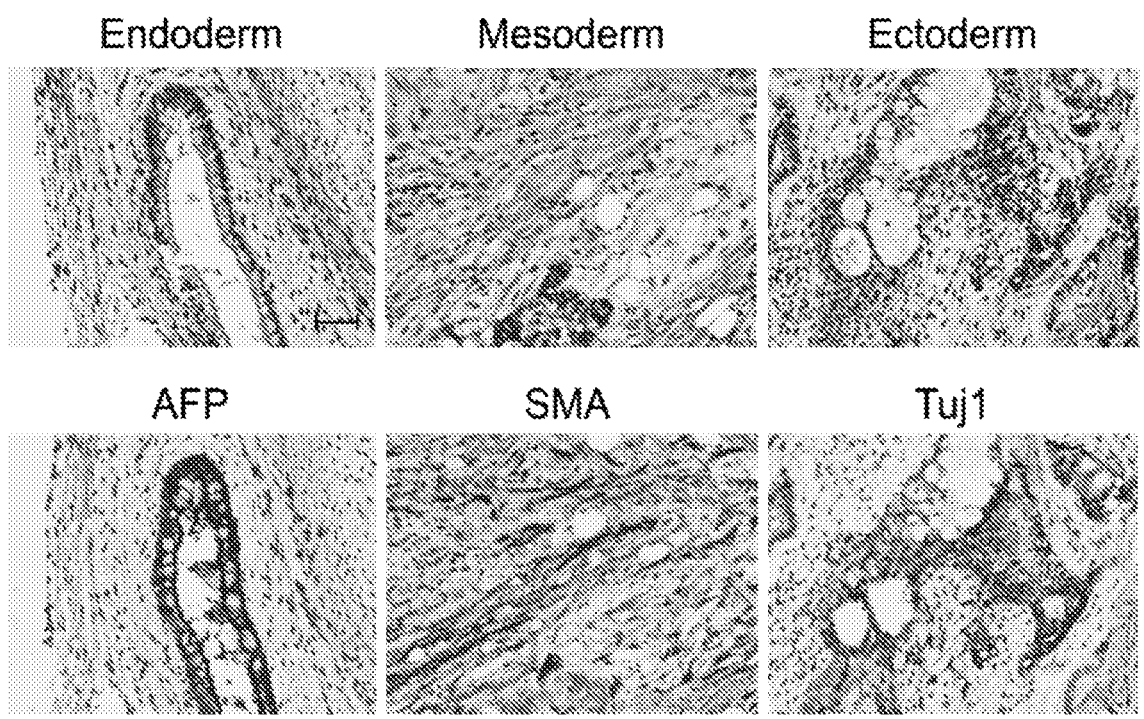
Figure 10:
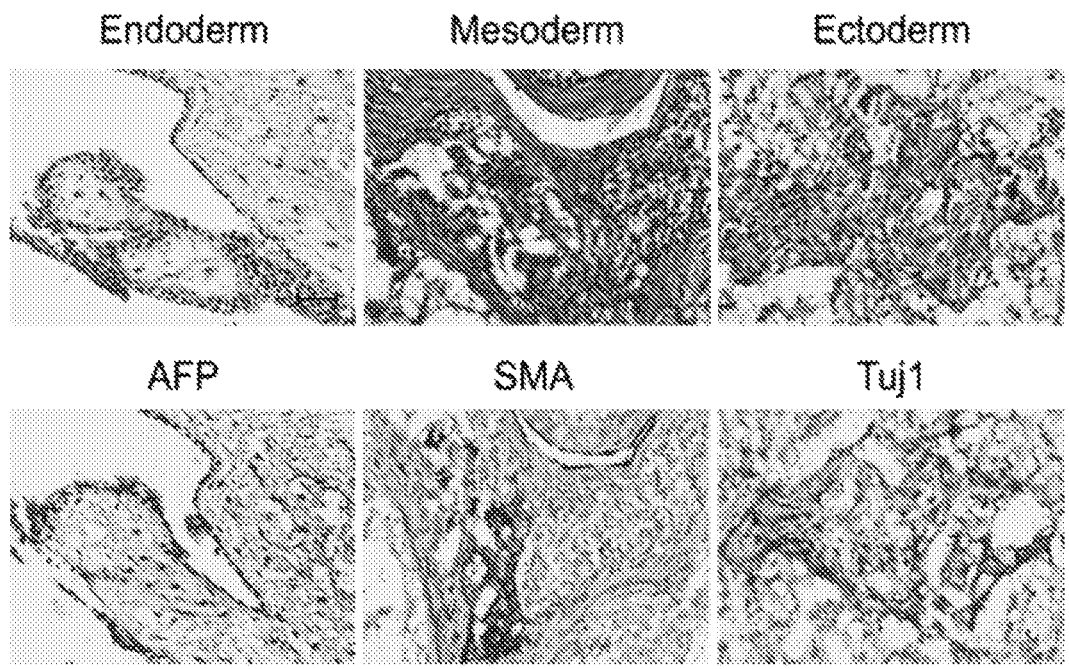
FIG. 10 shows that immunohistochemistry images of cardiac glycoside-treated teratomas. These images represent paraffin sections showing the three germ layer lineages of cardiac glycoside-treated teratomas. Digoxin-treated teratoma sections were stained with H&E (top panel) and underwent IHC staining for the three lineage markers (bottom panel). Lanatoside C-treated teratoma sections were stained with H&E (top panel) and underwent IHC staining for the three lineage markers (bottom panel). AFP (alpha-fetoprotein): endoderm marker. SMA (smooth muscle actin): mesoderm marker. Tuj1 (beta-III tubulin): ectoderm marker. Scale bar: 50 µm.
Figure 10:
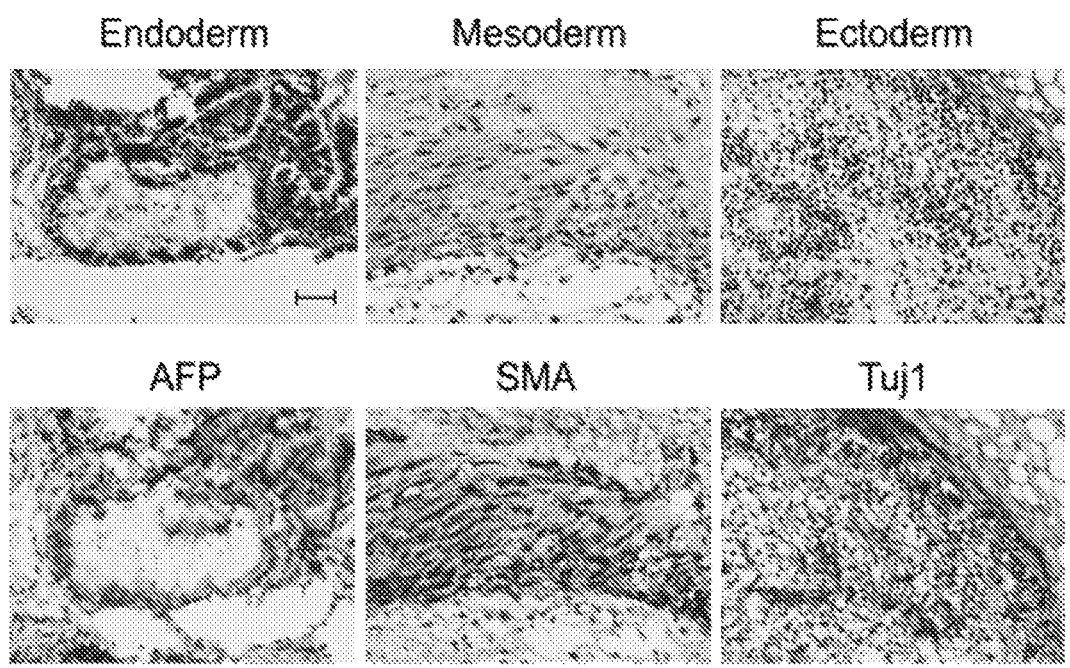

To investigate whether hESCs treated with cardiac glycosides lose their ability to form teratomas, hESCs were treated with DMSO, digoxin or lanatoside C and were transplanted into NSG mice individually for xenograft. We found that the tumor weight was significantly decreased in the cardiac glycoside drug-treated group (FIGS. 5A and 5B). Thus, digoxin and lanatoside C severely hampered most of the tumor formation ability in the hESCs. Teratoma formation in the DMSO-, digoxin-, or lanatoside C-treated hESCs was shown to contain all three germ layers (FIG. 5C and FIG. 10). These results demonstrate the pluripotent ability of these hESCs. We demonstrated that the cardiac glycosides efficiently prevented tumor formation in vivo.

Figure 11A:
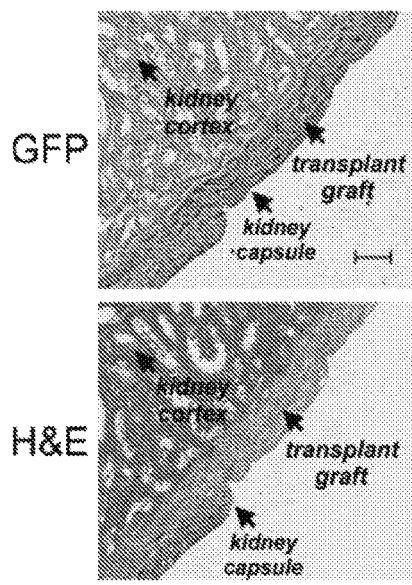
FIG. 11A to FIG. 11C include charts showing that drug-treated hBMMSCs remained in NSG mice after the cell transplantation.
Figure 11B:
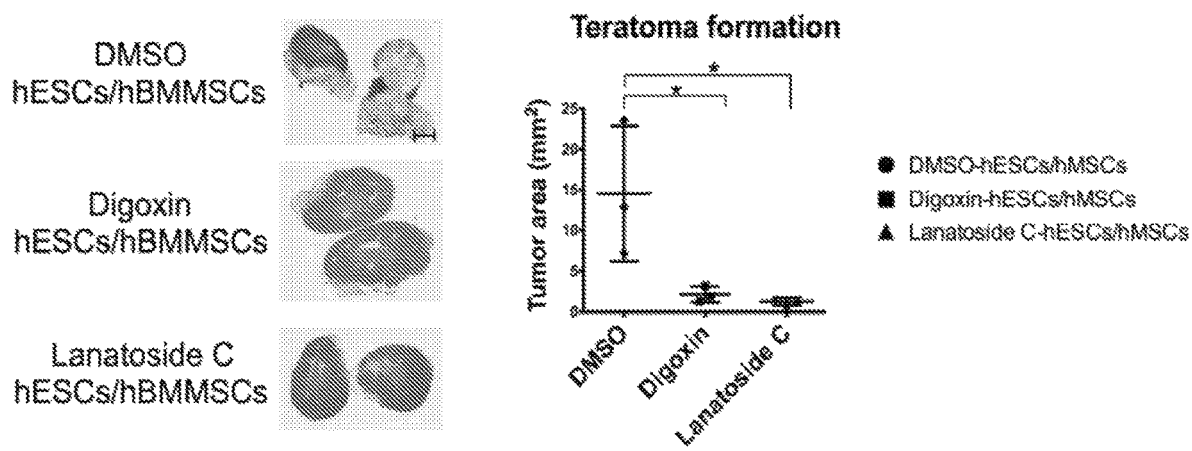
Figure 11C:
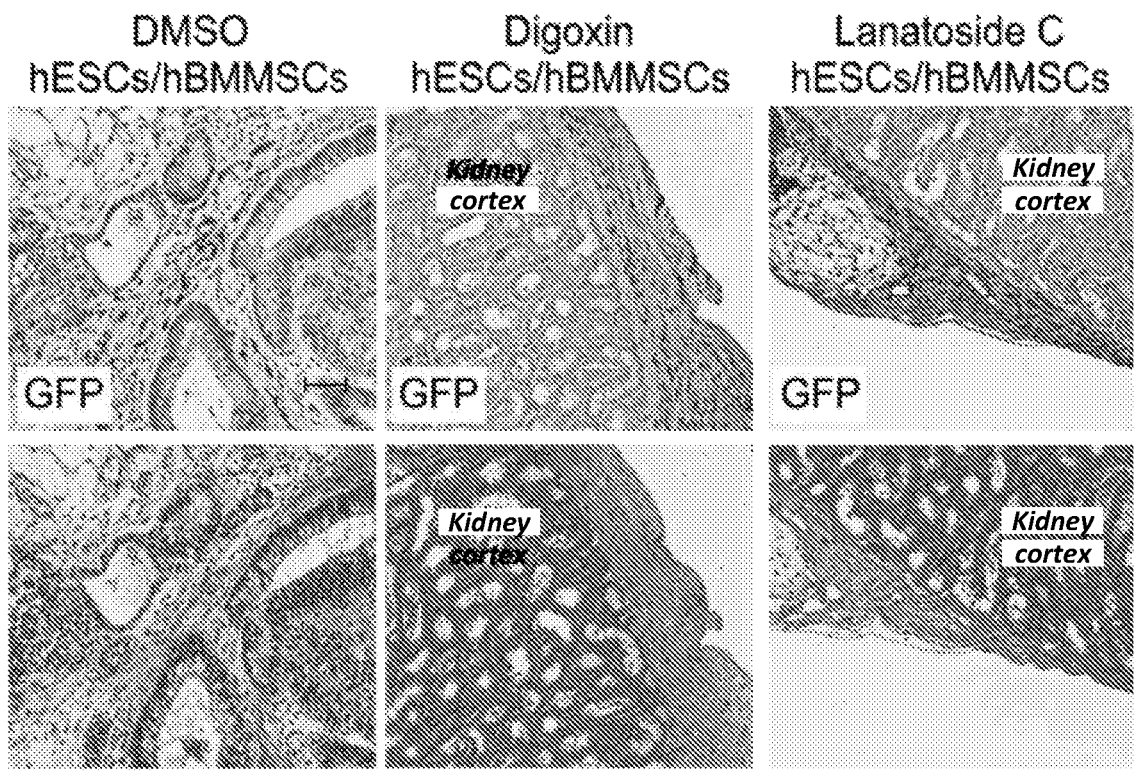

Finally, to investigate whether digoxin- or lanatoside C-treated hBMMSCs remain in vivo, we constructed GFP overexpressing hBMMSCs. The GFP overexpressing hBMMSCs did not form tumors in the NSG mice under the kidney capsules (FIG. 11A). The GFP-hBMMSCs remained at the graft site, which was observed by GFP IHC staining (FIG. 11A). Then, a mixture of hESCs and hBMMSCs that were treated with the drugs was injected into NSG mice under the kidney capsules. The tumor area was also significantly inhibited in the digoxin- or lanatoside C-treated groups (FIG. 11B), and we still observed GFP-positive hBMMSCs (FIG. 11C). These results demonstrated that digoxin- and lanatoside C-treated hBMMSCs remained in the NSG mice under the kidney capsules.

3. Summary and Discussion

In cell therapy, residual undifferentiated ESCs or iPSCs in their differentiated progenies raise concerns regarding the safety (teratoma) of using PSC-derived cells. The tumorigenic ability of undifferentiated PSCs is lost upon terminal differentiation. However, residual undifferentiated PSCs must be removed prior to the application of ESCs and iPSC cell therapy[40]. In this study, our data demonstrated the cytotoxicity effect of cardiac glycosides in hESCs (FIG. 1B, FIG. 1C, FIG. 2A, FIG. 2C, FIG. 6, FIG. 12). This phenomenon was not observed in the hBMMSCs (FIG. 1D, FIG. 1E, FIG. 2B, FIG. 2C). Most importantly, these drugs did not affect the stem cells differentiation abilities (FIG. 3). A similar effect of cardiac glycosides was shown in the hESC-derived progeny. The viability of the hESC-MSCs, hESC-neurons and hiPSC-endothelial cells were also not affected by digoxin and lanatoside C (FIG. 4, FIG. 9). Furthermore, the in vivo experiments showed that digoxin and lanatoside C efficiently prevented teratoma formation (FIG. 5). For the first time, our work described the cytotoxic effect and tumor prevention capabilities of cardiac glycosides in hESCs. Digoxin and lanatoside C are also the first FDA approved drugs that have been shown to have cytotoxicity in hESCs.

To overcome the risk of teratoma formation in regenerative medicine, several strategies have been proposed[41,42]. Antibody-sorting and cytotoxic antibody strategies may be simple, but their efficiency is limited due to single-cell dissociation requirements or antibody batch variations[7,17,18,43]. The cost of these approaches is also high. Another strategy is based on the genetic manipulation of traceable target cells[10,12,44,45], but these methods are laborious and expensive. Most importantly, insertion mutagenesis is a biosafety threat in the clinical use of such genetically altered cells[42]. Chemical ablation strategies are rapid, robust and efficient, and they are also the most cost-effective methods. Chemical approaches do not require cell sorting and any genetic manipulation.

Figure 4E:
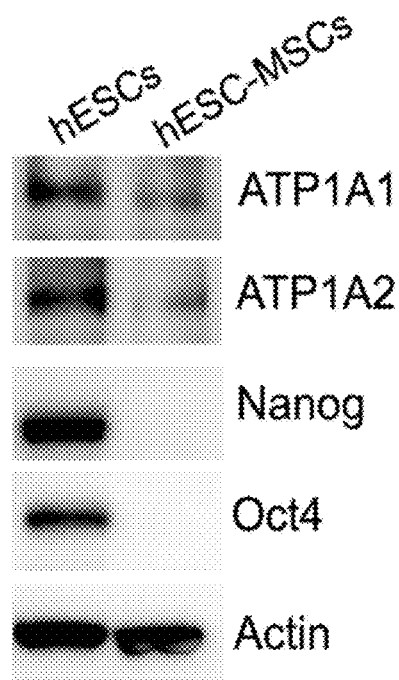

In addition to small molecule approaches, a study has used metabolic selection to enrich PSC-derived cardiomyocytes[13]. The authors provided an interesting method to purify cardiomyocytes from PSCs using glucose-depleted and lactate-rich culture conditions. This method is very suitable for generating high purity cardiomyocytes. However, other cell types might need more tests to determine the cell type specific metabolism. This strategy is attractive but can be applied in only a very few cell types. We used CG drugs to eliminate undifferentiated hESCs, and the drugs did not affect the survival of several different cell types (i.e., MSCs, endothelium cells, neurons). Since CGs is easy to purchase and are cost efficient, this method may be convenient for applications in the future. Digoxin and lanatoside C are potent small molecules that inhibit tumorigenic hESCs in culture as shown by the teratoma formation assay (FIG. 5). The expression levels of the $Na^+/K^+$-ATPase subunits were different between the cancer and normal cells or tissues[23]. Furthermore, our data suggested that the expression levels of the $Na^+/K^+$-ATPase subunits were also different between the undifferentiated and differentiated cells (FIG. 1A, FIG. 4E). In this study, we revealed a novel application of cardiac glycosides that may improve the major concern of hPSCs cell therapy by preventing teratoma formation.

REFERENCES

1 Ben-David, U., Kopper, O. & Benvenisty, N. Expanding the boundaries of embryonic stem cells. *Cell Stem Cell* 10, 666-677, doi:10.1016/j.stem.2012.05.003 (2012).

2 Knoepfler, P. S. Deconstructing stem cell tumorigenicity: a roadmap to safe regenerative medicine. *Stem cells (Dayton, Ohio)* 27, 1050-1056, doi:10.1002/stem.37 (2009).

3 Ben-David, U. & Benvenisty, N. The tumorigenicity of human embryonic and induced pluripotent stem cells. *Nat Rev Cancer* 11, 268-277, doi:10.1038/nrc3034 (2011).

4 Lee, A. S. et al. Effects of cell number on teratoma formation by human embryonic stem cells. *Cell Cycle* 8, 2608-2612, doi:10.4161/cc.8.16.9353 (2009).

5 Tan, H. L., Fong, W. J., Lee, E. H., Yap, M. & Choo, A. mAb 84, a cytotoxic antibody that kills undifferentiated human embryonic stem cells via oncosis. *Stem cells (Dayton, Ohio)* 27, 1792-1801, doi:10.1002/stem.109 (2009).

6 Choo, A. B. et al. Selection against undifferentiated human embryonic stem cells by a cytotoxic antibody recognizing podocalyxin-like protein-1. *Stem cells (Dayton, Ohio)* 26, 1454-1463, doi:10.1634/stemcells.2007-0576 (2008).

7 Tang, C. et al. An antibody against SSEA-5 glycan on human pluripotent stem cells enables removal of teratoma-forming cells. *Nat Biotechnol* 29, 829-834, doi: 10.1038/nbt.1947 (2011).

8 Ben-David, U., Nudel, N. & Benvenisty, N. Immunologic and chemical targeting of the tight-junction protein Claudin-6 eliminates tumorigenic human pluripotent stem cells. *Nat Commun* 4, 1992, doi:10.1038/ncomms2992 (2013).

9 Fong, C. Y, Peh, G. S., Gauthaman, K. & Bongso, A. Separation of SSEA-4 and TRA-1-60 labelled undifferentiated human embryonic stem cells from a heterogeneous cell population using magnetic-activated cell sorting (MACS) and fluorescence-activated cell sorting (FACS). *Stem Cell Rev* 5, 72-80, doi:10.1007/s12015-009-9054-4 (2009).

10 Blum, B., Bar-Nur, O., Golan-Lev, T. & Benvenisty, N. The anti-apoptotic gene survivin contributes to teratoma formation by human embryonic stem cells. *Nat Biotechnol* 27, 281-287, doi:10.1038/nbt.1527 (2009).

11 Menendez, S. et al. Increased dosage of tumor suppressors limits the tumorigenicity of iPS cells without affecting their pluripotency. *Aging cell* 11, 41-50, doi:10.1111/j.1474-9726.2011.00754.x (2012).

12 Schuldiner, M., Itskovitz-Eldor, J. & Benvenisty, N. Selective ablation of human embryonic stem cells expressing a "suicide" gene. *Stem cells (Dayton, Ohio)* 21, 257-265, doi:10.1634/stemcells.21-3-257 (2003).

13 Tohyama, S. et al. Distinct metabolic flow enables large-scale purification of mouse and human pluripotent stem cell-derived cardiomyocytes. *Cell Stem Cell* 12, 127-137, doi:10.1016/j.stem.2012.09.013 (2013).

14 Lee, M. O. et al. Inhibition of pluripotent stem cell-derived teratoma formation by small molecules. *Proceedings of the National Academy of Sciences of the United States of America* 110, E3281-3290, doi:10.1073/pnas.1303669110 (2013).

15 Ben-David, U. et al. Selective elimination of human pluripotent stem cells by an oleate synthesis inhibitor discovered in a high-throughput screen. *Cell Stem Cell* 12, 167-179, doi:10.1016/j.stem.2012.11.015 (2013).

16 Dabir, D. V. et al. A small molecule inhibitor of redox-regulated protein translocation into mitochondria. *Developmental cell* 25, 81-92, doi:10.1016/j.devcel.2013.03.006 (2013).

17 Baker, M. Reproducibility crisis: Blame it on the antibodies. *Nature* 521, 274-276, doi:10.1038/521274a (2015).

18 Prassas, I. & Diamandis, E. P. Translational researchers beware! Unreliable commercial immunoassays (ELISAs) can jeopardize your research. *Clin Chem Lab Med* 52, 765-766, doi:10.1515/cclm-2013-1078 (2014).

19 Egelhofer, T. A. et al. An assessment of histone-modification antibody quality. *Nat Struct Mol Biol* 18, 91-93, doi:10.1038/nsmb.1972 (2011).

20 Michel, M. C., Wieland, T. & Tsujimoto, G. How reliable are G-protein-coupled receptor antibodies? *Naunyn-Schmiedeberg's archives of pharmacology* 379, 385-388, doi:10.1007/s00210-009-0395-y (2009).

21 Blum, B. & Benvenisty, N. The tumorigenicity of human embryonic stem cells. *Adv Cancer Res* 100, 133-158, doi:10.1016/S0065-230X(08)00005-5 (2008).

22 Richards, M. et al. A new class of pluripotent stem cell cytotoxic small molecules. *PLoS One* 9, e85039, doi: 10.1371/journal.pone.0085039 (2014).

23 Prassas, I. & Diamandis, E. P. Novel therapeutic applications of cardiac glycosides. *Nat Rev Drug Discov* 7, 926-935, doi:10.1038/nrd2682 (2008).

24 Gheorghiade, M., Adams, K. F., Jr. & Colucci, W. S. Digoxin in the management of cardiovascular disorders. *Circulation* 109, 2959-2964, doi:10.1161/01.CIR.0000132482.95686.87 (2004).

25 Mijatovic, T. et al. Cardiotonic steroids on the road to anti-cancer therapy. *Biochim Biophys Acta* 1776, 32-57, doi:10.1016/j.bbcan.2007.06.002 (2007).

26 Diederich, M., Muller, F. & Cerella, C. Cardiac glycosides: From molecular targets to immunogenic cell death. *Biochem Pharmacol*, doi:10.1016/j.bcp.2016.08.017 (2016).

27 Thomson, J. A. et al. Embryonic stem cell lines derived from human blastocysts. *Science* 282, 1145-1147 (1998).

28 Cowan, C. A. et al. Derivation of embryonic stem-cell lines from human blastocysts. *N Engl J Med* 350, 1353-1356, doi:10.1056/NEJMsr040330 (2004).

29 Wang, C. H. et al. A shRNA functional screen reveals Nme6 and Nme7 are crucial for embryonic stem cell renewal. *Stem cells (Dayton, Ohio)* 30, 2199-2211, doi: 10.1002/stem.1203 (2012).

30 Wang, X. et al. Immune modulatory mesenchymal stem cells derived from human embryonic stem cells through a trophoblast-like stage. *Stem cells (Dayton, Ohio)* 34, 380-391, doi:10.1002/stem.2242 (2016).

31 Lai, P. L. et al. Efficient Generation of Chemically Induced Mesenchymal Stem Cells from Human Dermal Fibroblasts. *Sci Rep* 7, 44534, doi:10.1038/srep44534 (2017).

32 Hentze, H. et al. Teratoma formation by human embryonic stem cells: evaluation of essential parameters for future safety studies. *Stem Cell Res* 2, 198-210, doi: 10.1016/j.scr.2009.02.002 (2009).

33 Fischer, A. H., Jacobson, K. A., Rose, J. & Zeller, R. Hematoxylin and eosin staining of tissue and cell sections. *CSH Protoc* 2008, pdb prot4986, doi:10.1101/pdb.prot4986 (2008).

34 Wu, Y T. et al. Defining minimum essential factors to derive highly pure human endothelial cells from iPS/ES cells in an animal substance-free system. *Sci Rep* 5, 1-9, doi:10.1038/srep09718 (2015).

35 Wen, Z. et al. Synaptic dysregulation in a human iPS cell model of mental disorders. *Nature* 515, 414-418, doi: 10.1038/nature13716 (2014).

36 Hannan, N. R., Segeritz, C. P., Touboul, T. & Vallier, L. Production of hepatocyte-like cells from human pluripotent stem cells. *Nat Protoc* 8, 430-437 (2013).

37 Hyslop, L. et al. Downregulation of NANOG induces differentiation of human embryonic stem cells to extra-embryonic lineages. *Stem cells (Dayton, Ohio)* 23, 1035-1043, doi:10.1634/stemcells.2005-0080 (2005).

38 Wang, Z., Oron, E., Nelson, B., Razis, S. & Ivanova, N. Distinct lineage specification roles for NANOG, OCT4, and SOX2 in human embryonic stem cells. *Cell Stem Cell* 10, 440-454, doi:10.1016/j.stem.2012.02.016 (2012).

39 Pittenger, M. F. et al. Multilineage potential of adult human mesenchymal stem cells. *Science* 284, 143-147 (1999).

40 Nishikawa, S., Goldstein, R. A. & Nierras, C. R. The promise of human induced pluripotent stem cells for research and therapy. *Nat Rev Mol Cell Biol* 9, 725-729, doi:10.1038/nrm2466 (2008).

41 Ben-David, U. & Benvenisty, N. Chemical ablation of tumor-initiating human pluripotent stem cells. *Nat Protoc* 9, 729-740, doi:10.1038/nprot.2014.050 (2014).

42 Rashin, M., Amir, A. H. & Javad, V. a. A., S.-H. Safe transplantation of pluripotent stem cell by preventing teratoma formation. *Journal of Stem Cell Research & Therapy* 4, doi:10.4172/2157-7633.1000212 (2014).

43 Schriebl, K. et al. Selective removal of undifferentiated human embryonic stem cells using magnetic activated cell sorting followed by a cytotoxic antibody. *Tissue Eng Part A* 18, 899-909, doi:10.1089/ten.TEA.2011.0311 (2012).

44 Chung, S. et al. Genetic selection of sox1GFP-expressing neural precursors removes residual tumorigenic pluripotent stem cells and attenuates tumor formation after transplantation. *J Neurochem* 97, 1467-1480, doi: 10.1111/j.1471-4159.2006.03841.x (2006).

Huber, I. et al. Identification and selection of cardiomyocytes during human embryonic stem cell differentiation. *FASEB J* 21, 2551-2563, doi:10.1096/fj.05-5711com (2007).

What is claimed is:

1. A method for removing undifferentiated pluripotent stem cells from a sample comprising said cells, the method comprising exposing said samples to an effective amount of a cardiac glycoside, wherein the sample further comprises differentiated cells, in which said differentiated cells are mesenchymal stem cells (MSCs) or said differentiated cells are selected from the group consisting of osteoblasts, adipocytes, chondrocytes, endothelial cells, neuron cells and hepatocytes, and wherein the cardiac glycoside is a compound selected from the group consisting of:

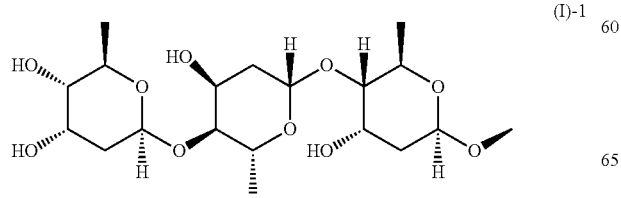

(I)-1

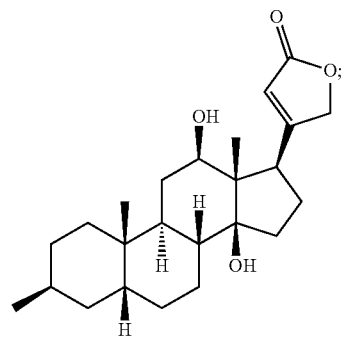

(digoxin)

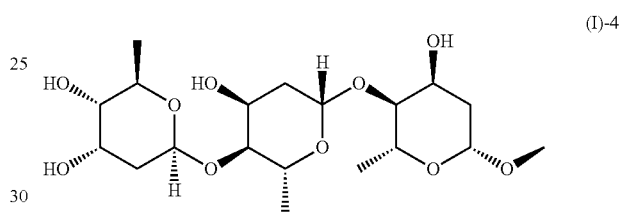

(I)-4

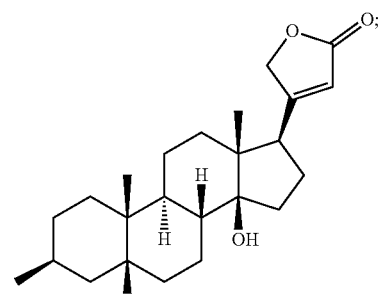

(digitoxin)

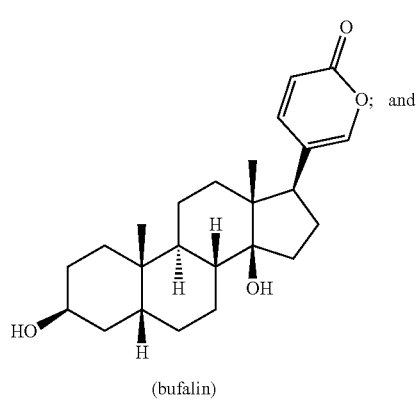

(I)-6

(bufalin)

33

-continued

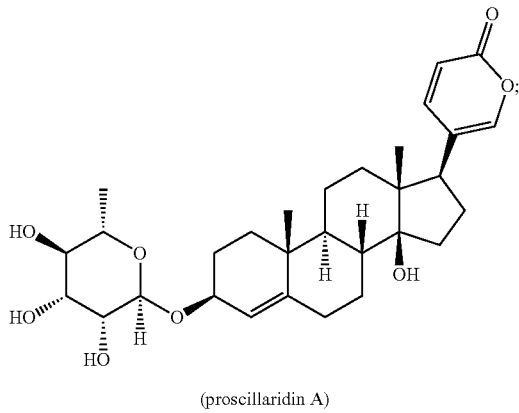

(proscillaridin A) (I)-7 or a pharmaceutical acceptable salt thereof.

2. The method of claim 1, wherein the undifferentiated pluripotent stem cells are selected from the group consisting of embryonic stem cells (ESCs) and induced pluripotent stem cells (IPSC).

3. The method of claim 1, wherein the undifferentiated pluripotent stem cells express a cell marker selected from

34 the group consisting of $Na^+/K^+$-ATPase, Nanog, Oct4, Sox2, SSEA3, SSEA4, TRA-1-60, TRA-1-81 and a combination thereof.

4. The method of claim 1, wherein the differentiated cells are mesenchymal stem cells (MSCs).

5. The method of claim 4, wherein the differentiated cells express a cell marker selected from the group consisting of consisting of $CD44^+$, $CD73^+$, $CD90^+$, $CD105^+$ and a combination thereof.

6. The method of claim 5, wherein the differentiated cells are $CD45^-$, $CD34^-$, $CD11b^-$, $CD19^-$, and/or $HLA-DR^-$.

7. A method for preparing differentiated cells, comprising
(i) subjecting undifferentiated pluripotent stem cells to a condition suitable for differentiation to produce a cell population that comprises differentiated cells and undifferentiated pluripotent stem cells, wherein said differentiated cells are mesenchymal stem cells (MSCs) or wherein said differentiated cells are selected from the group consisting of osteoblasts, adipocytes, chondrocytes, endothelial cells, neuron cells and hepatocytes;
(ii) removing the undifferentiated pluripotent stem cells by exposing the cell population to an effective amount of a cardiac glycoside;
wherein the cardiac glycoside is a compound selected from the group consisting of:

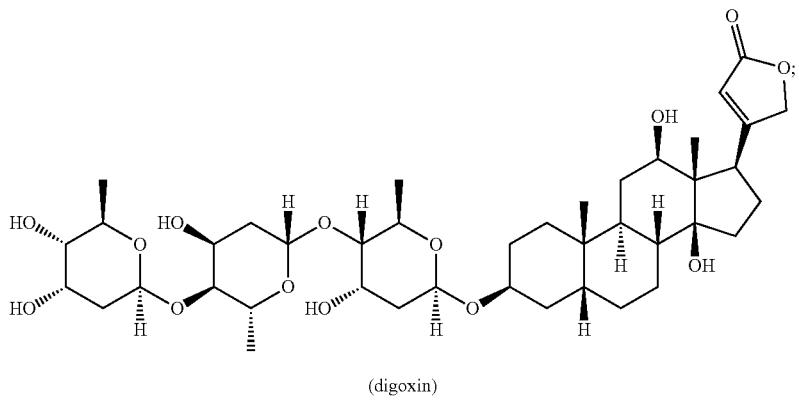

(digoxin) (I)-1

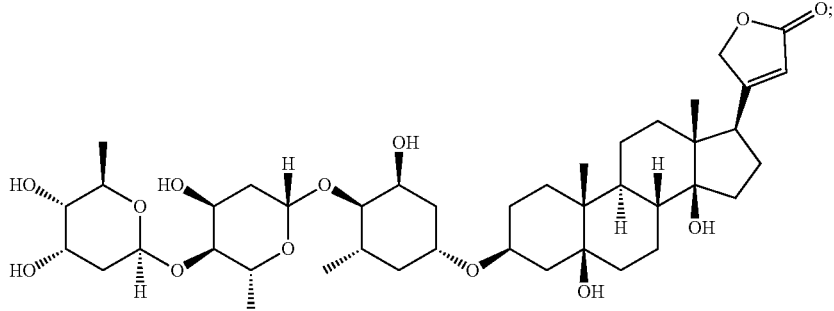

(digitoxin) (I)-4

-continued

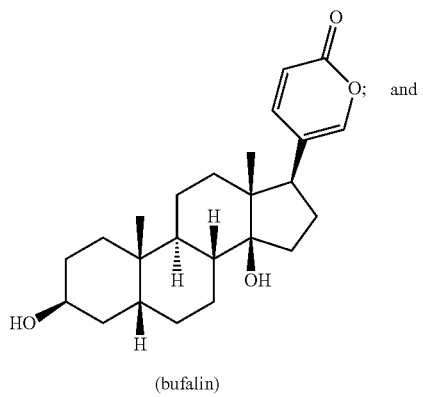

(bufalin)

(I)-6

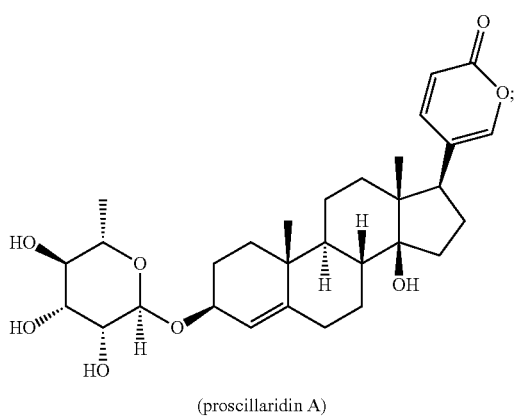

(proscillaridin A)

(I)-7 or a pharmaceutical acceptable salt thereof.

8. The method of claim 7, wherein the undifferentiated pluripotent stem cells are selected from the group consisting of embryonic stem cells (ESCs) and induced pluripotent stem cells (IPSC).

9. The method of claim 7, wherein the differentiated cells are mesenchymal stem cells (MSCs).

10. The method of claim 9, wherein the differentiated cells express a cell marker selected from the group consisting of consisting of CD44$^+$, CD73$^+$, CD90$^+$, CD105$^+$ and a combination thereof.

11. The method of claim 10, wherein the differentiated cells are CD45$^-$, CD34$^-$, CD11b$^-$, CD19$^-$, and/or HLA-DR.

* * * * *